US006455299B1

(12) United States Patent
Steinman et al.

(10) Patent No.: US 6,455,299 B1
(45) Date of Patent: Sep. 24, 2002

(54) METHODS OF USE OF VIRAL VECTORS TO DELIVER ANTIGEN TO DENDRITIC CELLS

(75) Inventors: Ralph M. Steinman, Westport, CT (US); Nina Bhardwaj, West Orange, NJ (US)

(73) Assignee: The Rockefeller University, New York, NY (US)

(*) Notice: Subject to any disclaimer, the term of this patent is extended or adjusted under 35 U.S.C. 154(b) by 0 days.

(21) Appl. No.: 09/310,560

(22) Filed: May 12, 1999

Related U.S. Application Data

(62) Division of application No. 08/693,586, filed on Aug. 1, 1996, now Pat. No. 6,300,090, which is a continuation of application No. 08/282,996, filed on Jul. 29, 1994, now abandoned.

(51) Int. Cl.[7] .............................. C12N 7/00; C12N 5/08
(52) U.S. Cl. .................................... 435/235.1; 435/372
(58) Field of Search ........................ 435/6, 235.1, 325, 435/69.3, 455, 372; 536/23.1

(56) References Cited

U.S. PATENT DOCUMENTS 5,846,827 A * 12/1998 Celis et al. .................. 435/384
5,851,756 A * 12/1998 Steinman et al. ............... 435/2

OTHER PUBLICATIONS

Macatonia et al. Primary proliferative and cytotoxic T–cell responses to HIV induced in vitro by human denedritic cells. Immunol. Vo. 74:399–406, Oct. 1991.*
Macatonia et al. Primary stimulation by dendritic cells induces antiviral proliferative and cytotoxic T cell responses in vitro. J. Exp. Med. vol. 169:12255–64, Apr. 1989*
Bhardwaj, et al. Influenza virus–infected dendritic cells stimulate strong proliferative and cytolytic responses from human CD8 T cells. J. Clin. Invest. vol. 94:797–807, Aug. 1994.*
Nonacs et al. Mechanisms of mouse spleen dendritic cell function in the generation of influenza–specific, cytolytic T lymphocytes. J. Exp. Med. vol. 176:519–529, Aug. 1992.*
Agger, et al., "Two Populations of Splenic Dendritic Cells Detected with M342, A New Monoclonal to an Intracellular Antigen of Interdigitating Dendritic Cells and Some B Lymphocytes." *J. Leukocyte Biol.* 52:34–42. 1992.
Bakker, et al., "Generation of Antimelanoma Cytotoxic T Lymphocytes From Healthy Donors After Presentation of Melanoma–Associated Antigen–Derived Eptiopes by Dendritic Cells in Vitro." *Cancer Research*, vol. 55, pp. 5330–5334, Nov. 15, 1995.
Bender, et al. "Inactivated Influenza Virus, when presented on Dendritic Cells, Elicit Human CD8[+]Cytolytic T Cell Responses." *J. Exp. Med.*, vol. 182, pp. 1663–1671, Dec., 1995.

Enami, et al., "Introduction of Site–Specific Mutations Into the Genome of Influenza Virus" PNAS vol. 87/10:3802–3805 May 1990.
Francotte, et al., "Enhancement of Antibody Response by Mouse Dendritic Cells Pulsed with Tobacco Mosaic Virus or with Rabbit Antidiotypic Antibodies Raised Against a Private Rabbit Idiotype", *Proc. Natl. Acad. Sci. USA*, vol. 82, Dec. 1985, pp. 8149–8152.
Hosaka, et al., Entry of Heat–inactivated Influenza Virus and Induction of Target Susceptibility To Cytotoxic T Cell–Mediated Lysis, *Virus Res.*, Suppl. 1, p. 56, 1985.
Inaba, et all, "Dendritic Cells Pulsed with Protein Antigens in vitro can Prime Antigen–Specific, MCH–Restricted T Cells in situ", *J. Exp. Med.*, Aug., 1990, vol. 172, pp. 631–640.
Inaba, et al. "Protein Specific Helper T–Lymphocyte Formation Initiated by Dendritic Cells", *Science*, Aug. 2, 1985, vol. 229, No. 4713, pp. 475–479.
Inaba et al. "Clustering of Dendritic Cells, Helper T Lymphocytes, and Histocompatible B Cells During Primary Antibody Responses in vitro", *J. Exp. Med.*, Sep., 1984, vol. 160, No. 3, pp. 858–876.
Inaba, et al., "Properties of Memory T Lymphocytes Isolated from the Mixed Leukocyte Reaction", *Proc. Natl. Acad. Sci. USA*, Nov. 1985, vol. 82, No. 22, pp. 7686–7690.
Inaba, et al., "Resting and Sensitized T Lymphocytes Exhibit Distinct Stimulatory (Antigen–Presenting Cell) Requirements for Growth and Lymphokine Release", *J. Exp. Med.*, vol. 160, No. 6, Dec. 1, 1984, pp. 1717–1735.
Inaba, et al., "The Function of IA+ Dendritic Cells and IA Dendritic Cell Precursors in Thymocyte Mitogenesis to Lectin and Lectin Plus Interleukin 1" *J. Exp. Med.*, vol. 167, Jan. 1988, pp. 149–162.
Inaba, et al. "Generation of Large Numbers of Dendritic Cells from Mouse Bone Marrow Cultures Supplemented with Granulocyte/Macrophage Colony–Stimulating Factor", *J. Exp. Med.*, vol. 176, No. 6, Dec., 1992, pp. 1693–1702.
Iwai, et al. "Acceptance of Murine Thyroid Allografts by Pretreatment of Anti–IA Antibody or Anti–Dendritic Cell Antibody in vitro", *Transplantation*, vol. 47, No. 1, Jan., 1989, pp. 45–49.

(List continued on next page.)

*Primary Examiner*—Remy Yucel
*Assistant Examiner*—William Sandals
(74) *Attorney, Agent, or Firm*—Morgan & Finnegan, L.L.P.

(57) ABSTRACT

This invention relates to methods and compositions useful for delivering antigens to dendritic cells which are then useful for inducing T antigen specific cytotoxic T lymphocytes. This invention also provides assays for evaluating the activity of cytotoxic T lymphocytes. According to the invention, antigens are provided to dendritic cells using a viral vector such as influenza virus which may be modified to express non-native antigens for presentation to the dendritic cells. The dendritic cells which are infected with the vector are then capable of presenting the antigen and inducing cytotoxic T lymphocyte activity or may also be used as vaccines.

11 Claims, 14 Drawing Sheets

OTHER PUBLICATIONS

Jansen, "Inhibition of Human Macrophage Colony Formation by Interleukin–4", *J. Exp. Med.*, vol. 170, Aug. 1989, pp. 577–582.

Jensen, P.E., "Protein Synthesis in Antigen Processing", *The Journal of Immunology*, vol. 141, No. 8, Oct. 15, 1988, pp. 2545–2550.

Klinkert, et al., "Accessory and Stimulating Properties of Dendritic Cells and Macrophages Isolated from Various Rat Tissues", *J. Exp. Med.*, vol. 156, No. 1, Aug. 1, 1982, pp. 1–19.

Knight, et al., "Induction of Immune Responses in vivo with Small Numbers of Veiled (Dendritic) Cells", *Proc.Natl.Acad.Sci.USA*, vol. 80, No. 19, Oct., 1983, pp. 6032–6035.

Knight, et al., "Role of Veiled Cells in Lymphocyte Activation", *European J. Immunology*, vol. 12, (1982), pp. 1057–1060.

Koch, et al., "Tumor Necrosis Factor α Maintains the Viability of Murine Epidermal Langerhans Cells in Culture, but in contrast to Granulocyte/Macrophage Colony–Stimulating Factor, without Inducing their Functional Maturation," *J. Exp. Med.*, vol. 171, No. 1, Jan. 1, 1990, pp. 159–171.

Kraal, et al., Langerhans' Cells Veiled Cells, and Interdigitating Cells in the Mouse Recognized by a Monoclonal Antibody, *J. Exp. Med.*, vol. 163, No. 4, Apr. 1, 1986, pp. 981–997.

The Lancet, "Peripheral Stem Cells Made to Work," Mar. 14, 1992, vol. 339, pp. 648–649.

Lanzavecchia, "Identifying Strategies for Immune Intervention", *Science*, vol. 260, May 14, 1993.

Lechler, et al., Restoration of Immunogenicity to Passenger Cell–Depleted Kidney Allografts by the Addition of Donor Strain Dendritic Cells, *J. Exp. Med.*, vol. 155, Jan., 1982, pp. 31–41.

Li, et al., "Priming with Recombinant Influenza Virus followed by Administration of Recombinant Vaccinia Virus Induces CD8+ T–Cell–Mediated Protective Immunity Against Malaria," *Proc. Natl. Acad. Sci. USA*, vol. 90, pp. 5214–5218, Jun. 1993.

Li, et al., "Influenza a Virus Transfectants with Chimeric Hemagglutinins Containing Epitopes From Diffrrent Subtypes", *Journal of Virology*, vol. 66, No. 1., pp. 399–404, Jan. 1992.

Luytjes, et al., "Amplification, Expression, and Packaging of a Foreign Gene by Influenza Virus", *Cell*, vol. 59, pp 1107–1113, Dec. 22, 1989.

Macatonia, et al., "Localization of Antigen on Lymph Node Dendritic Cells after Exposure to the Contact Sensitizer Fluorescein Isothiocyanate", *J.Exp.Med.*, vol. 166, Dec. 1987, pp. 1654–1667.

MacPherson, "Lymphoid Dendritic Cells: Their Life History and Roles in Immune Responses", *Res. Immunology* 1989, vol. 140, pp. 877–926.

Mukherji, et al., "Induction of Antigen–Specific Cytolytic T Cells in situ in Human Melanoma by Immunization with Synthetic Peptide–Pulsed Autologous Antigen Presenting Cells", *Proc. Natl. Acad. Sci., USA*, vol. 92, pp. 8078–8082, Aug. 1995.

Muster, et al., "An Influenza a Virus Containing Influenza B Virus 5' and 3' Noncoding Regions on the Neuraminidase Gene is attenuated in mice" vol. 88, pp. 5177–5181 Jun. 1991 PNAS.

Nair, et al, *J Virol* 67:4062–4069 1993.

Nixon–George, "The Adjuvant Effect of Stearyl Tyrosine on a Recombinant Subunit Hepatitis B Surface Antigen", *The Journal of Immunology*, vol. 144, No. 12, Jun. 15, 1990, pp. 4798–4802.

O'Doherty, et al., Dendritic Cells Freshly Isolated from Human Blood . . . : *J. Exp. Med.* : vol. 178: pp. 1067–1078 Sep. 1993.

O'Doherty, "Human Blood Contains Two Subsets of Dendritic Cells, One Immunologically Mature and the Other Immature", *Immunology*, vol. 82, 1994, pp. 487–493.

Osband, et al., Problems in the Investigational Study and Clinical Use of Cancer Immunotherapy, *Immunology Today*, vol. 11, No. 6, pp. 103–105, 1990.

Paglia, et al., "Immortalized Dendritic Cell Line Fully Competent in Antigen Presentation Initiates Primary T Cell Responded in vivo", *J. Exp. Med.*, vol. 178, Dec., 1993, pp. 1893–1901.

Peace, et al., "Lysis of Ras Oncogene–Transformed Cells by Specific Cytotoxic T Lymphocytes Elicited By Primary in vitro Immunization with Mutated Ras Peptide", *J. Exp. Med.*, vol. 179, Feb. 1994, pp. 473–479.

Pettengell, et al., "Peripheral Blood Progenitor Cell Transportation in Lymphoma and Leukemia using a Single Apheresis", *Blood*, vol. 82, No. 12, Dec. 15, 1993, pp. 3770–3777.

Ria, et al., "Immunological Activity of Covalently Linked T–Cell Epitopes", *Nature*, vol. 343, Jan. 25, 1990, pp. 381–383.

Romani, et al., "Generation of Mature Dendritic Cells from Human Blood. An Improved Method with Special Regard to Clinical Applicability", *J. Immunological Methods*, vol. 196, 1996, pp. 137–151.

Romani, N., et al., Presentation of Exogenous Protein Antigens by Dendritic Cells To T Cell Clones: Intact Protein is presented best by Immature Epidermal Langerhans Cells. J. Exp. Med. 169, 1169. (1989A.

Romani, et al., "Proliferating Dendritic Cell Progenitors in Human Blood", *J. Exp. Med.*, vol. 180, Jul. 1994, pp. 83–93.

Rudensky, et al., "Sequence Analysis of Peptides Bound to MCH Class II Molecules", *Nature*, vol. 353, Oct. 17, 1991, pp. 622–627.

Sallusto, et al., "Efficient Presentation of Soluble Antigen by Cultured Human Dendritic Cells is Maintained by Granulocyte/Macrophage Colony–Stimulating Factor Plus Interleukin 4 and Downregulated by Tumor Necrosis Factor α", *J. Exp. Med.*, vol. 179, Apr. 1994, pp. 1109–1118.

Scheicher, et al., "Dendritic Cells from Mouse Bone Marrow: In vitro Differentiation Using Low Doses of Recombinant Granulocyte–Macrophage Colony–Stimulating Factor", *J. Immunological Methods*, vol. 154, No. 2, pp. 253–264, 1991.

Schuler, et al., "Epidermal Langerhans Cells Represent Immature Dendritic Cells that Must Differentiate Prior to Expressing their Full Immunologic Potential", *Investig. Dermatology*, vol. 87, No. 1, Jul. 1, 1986, p. 166.

Schuler, et al., "Murine Epidermal Langerhans Cells Mature Into Potent Immunostimulatory Dendritic Cells in vitro", *J. Exp. Med.*, vol. 161, Mar. 1985, pp. 526–546.

Shimonkevitz, et al., "Antigen Recognition by H–2 Restricted T Cells", *J. Exp. Med.*, vol. 158, Aug. 1983, pp. 303–316.

Sornasse, et al., "Loading of Dendritic Cells with Antigen in vitro or in vivo by Immunotargeting can replace the Need for Adjuvant", *Adv. Exp. Med. Biol.*, vol. 329, 1993, pp. 299–303.

Steinman, "The Dendritic Cell System and its Role in Immunogenicity", *Ann. Rev. Immunology*, vol. 9, pp. 271–296, 1991.

Steinman, et al., Identification of a Novel Cell Type in Peripheral Lymphoid Organs of Mice, *J. Exp. Med.*, vol. 149, No. 2, pp. 1–16, Feb. 1979.

Steinman, et al., "Maturation and Migration of Cutaneous Dendritic Cells", *Investig. Dermatology*, vol. 105, No. 1, Jul. 1995, P. 2S–7S.

Steinman, et al., "Identification of a Novel Cell Type in Peripheral Lymphoid Organs of Mice", *J. Exp. Med.*, vol. 137, No. 4, Apr. 1, 1973, pp. 1142–1162.

Steinman, "Dendritic Cells: Clinical Aspects", *28th Forum in Immunology*, Rockefeller Univ. and Irvington. Inst. For Med. Res., pp. 911–924.

* cited by examiner

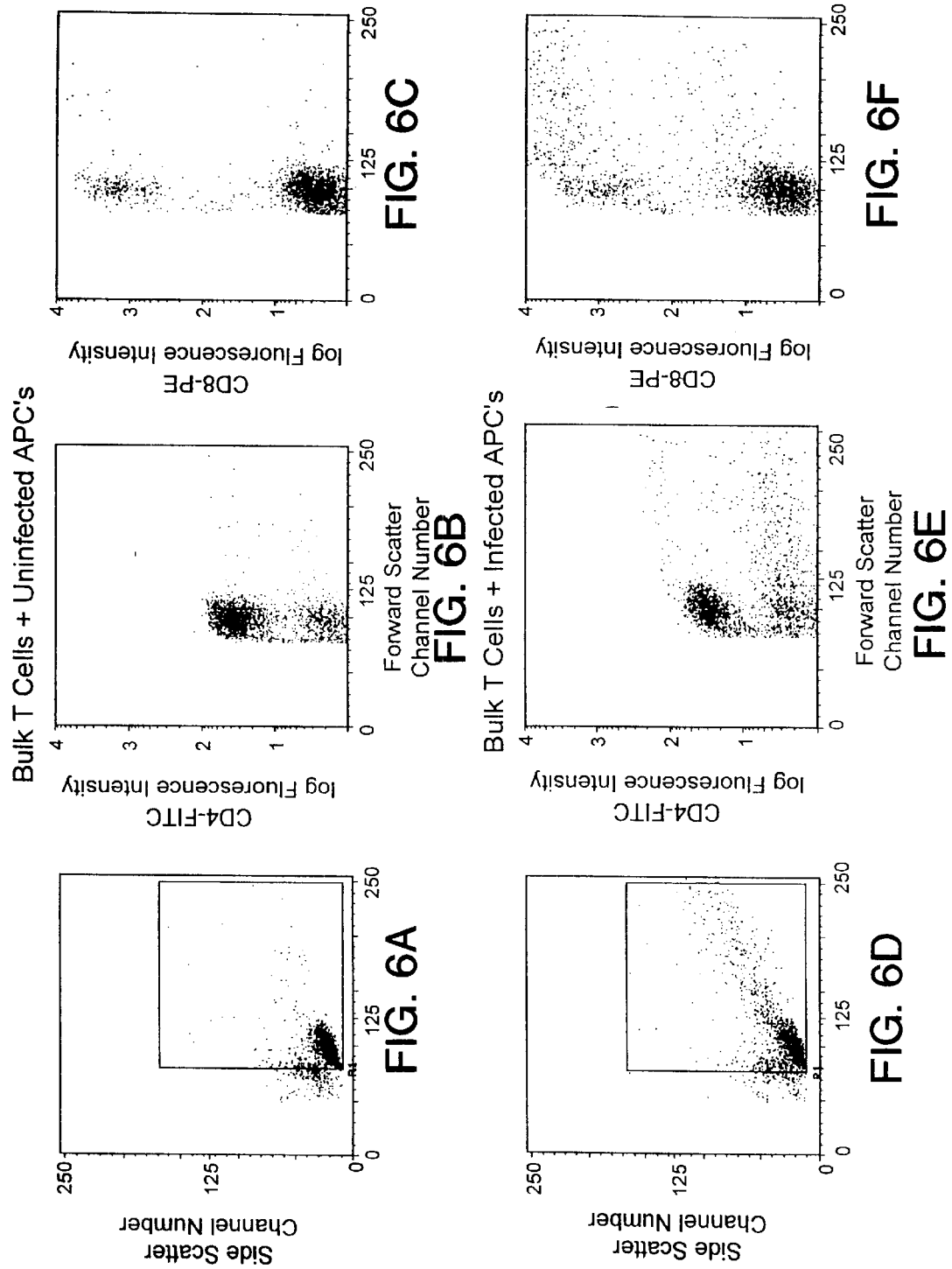

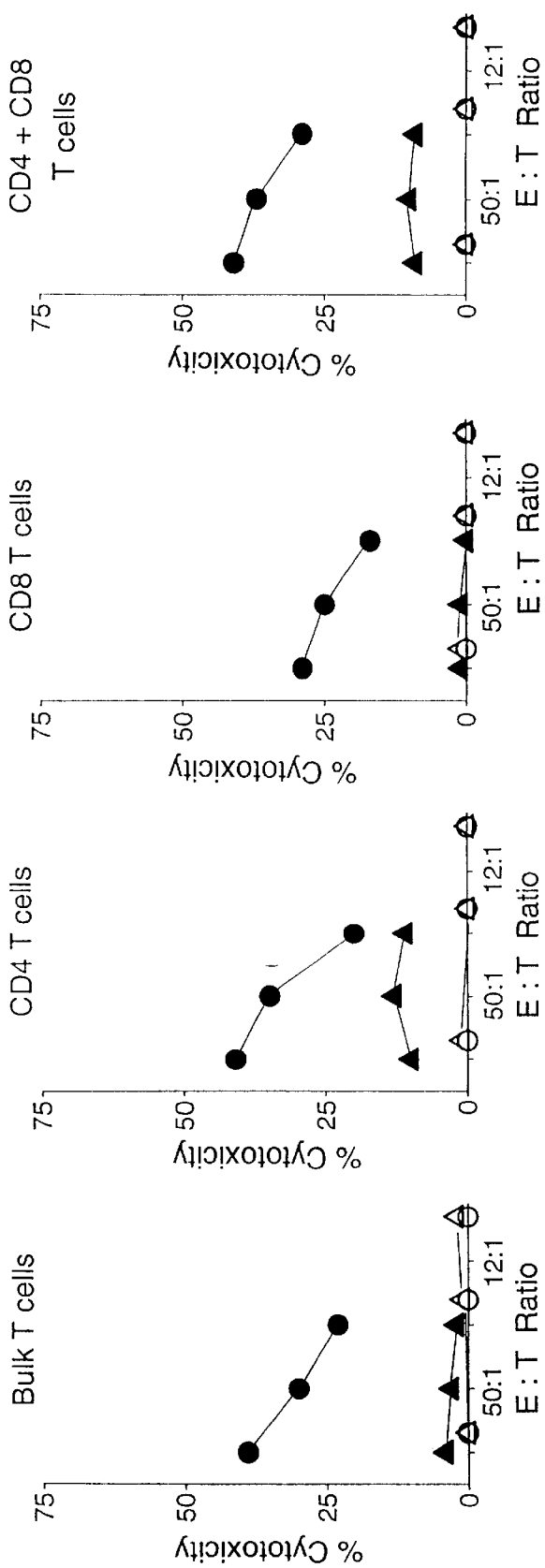

METHODS OF USE OF VIRAL VECTORS TO DELIVER ANTIGEN TO DENDRITIC CELLS

This is a divisional of application Ser. No. 08/693,586 filed Aug. 1, 1996 now U.S. Pat. No. 6,300,090 which is a continuation of application Ser. No. 08/282,996, filed Jul. 29, 1994 now abandoned.

This invention was made with United States Government support under National Institutes of Health grants AR-39552 and AI-24775. The United States Government has certain rights in this invention.

FIELD OF THE INVENTION

This invention relates to targeted antigen presentation in the immune system. More specifically, this invention relates to the use of viral vectors to deliver antigens to dendritic cells for processing and presentation to the immune system. This invention also relates to methods and compositions having preventive, diagnostic and therapeutic applications.

BACKGROUND OF THE INVENTION

The potential role of CD8+, cytolytic T lymphocytes [CTLs] in resistance to infectious and malignant diseases has been emphasized by recent developments in immunology. Antigen-specific CTLs are recognized as a possible defense mechanism in infection with HIV-1 (1-3), cytomegalovirus (4), and in malaria (5). Antigens that are recognized by melanoma-specific CTLS also have been identified by Boone and colleagues (6,7). These studies document the specificity of CTLs that recognize clinically important targets. Less is understood about the initial generation of these CTLs, however.

As in most T cell responses, the precursors for active CTLs are quiescent lymphocytes that must be induced to expand clonally and develop effector functions. For CTL activation to occur, not only must antigens be presented as peptide fragments on MHC products, but the antigen-MHC complexes must also be introduced on cells with the requisite accessory functions that lead to T cell growth and cytolytic activity. Studies of killer cells response to transplantation antigens, provide evidence that an effective way to induce human CTLs is to present antigens on dendritic cells (8). Dendritic cells are specialized accessory cells for the initiation of many T cell dependent immune responses [reviewed in (9)].

T cell receptors on $CD8^+$ T cells recognize a complex consisting of an antigenic peptide, $\beta$-2 microglobulin and Class I major histocompatibility complex (MHC) heavy chain (HLA-A, B, C, in humans). Processing and presenting of peptides on dendritic cells involves digesting of endogenously synthesized proteins and transporting them into the endoplastic reticulum, bound to Class I MHC heavy chain and $\beta$-2 microglobulin, and finally expressing the digested peptide in the cell surface in the groove of the Class I MHC molecule. Therefore, T cells can detect molecules that originate from proteins inside cells, in contrast to antibodies that detect intact molecules expressed on the cell surface. Consequently, CD8+ CTL are able to kill clinically important targets such as virus infected cells, tumors, and certain tissues attacked during autoimmune diseases.

Dendritic cells are potent antigen presenting cells for several immune responses. When exposed to replicating influenza virus, mouse dendritic cells stimulate strong cytolytic responses from CD8+ T cells. Prior work had not identified underlying mechanisms particularly the efficiency with which influenza virus infect dendritic cells, and whether the dendritic cells remain viable after exposure to influenza. Accordingly, it would be describe to identify mechanisms to deliver antigen on dendritic cell Class I molecules for presentation to CD8+ CTLs.

The proficiency of dendritic cells as APCs has been attributed to their ability to aggregate antigen responsive T cells into clusters, high expression of MHC Class I and Class II molecules, as well as adhesion and co-stimulatory molecules, and efficient endocytic activity for the MHC Class II pathway. Dendritic cells can sensitize quiescent human T cells when few MHC Class II molecules are occupied by antigen [a maximum of 0.1% of surface MHC Class II molecules or 2000 molecules], indicating that low levels of signal when presented on dendritic cells, are sufficient to generate T cell responses. However, the efficiency with which dendritic cells handle Class I restricted antigens is not known, one difficulty being the need to identify dendritic cell antigens which are Class I.

The development of new strategies in immunotherapy for treatment of cancers and pathogens is greatly needed. In particular, improved mechanisms for prophylaxis and therapy are needed in influenza, since control of the respiratory infection is not readily achieved through current approaches to vaccination. For example, presently available vaccines are not designed to induce killer cells but instead boost antibody responses to viral antigens that undergo antigenic drift and shift (10). It is known that dendritic cells are a component of the alveolar septae and airway epithelium of the lung (11,12), and that the appearance of influenza virus-specific CTLs is associated with a more rapid clearance of virus from nasal washings (13).

Influenza virus is also an agent used to dissect the different pathways for antigen presentation of dendritic cells and analyze the specificity of CTLS. Townsend et al. reported that viral proteins were processed in the dendritic cell cytoplasm and presented as peptides in association with Class I MHC products of the infected cell (14,15). Morrison et al. used influenza virus to distinguish two pathways for antigen presentation to CTLs (16). One emanates from acidic endocytic vesicles and leads to presentation on MHC Class II to CD4+ CTLs; the other emanates from a nonacidic biosynthetic compartment for presentation on MHC Class I to CD8+ CTLs.

There is considerable evidence, primarily in mouse cell cultures, that dendritic cells effectively present viral antigens to T cells (26,28–30). Murine dendritic cells can be infected by influenza virus and elicit potent CTL responses (26,29). The responses are dependent upon the synthesis of endogenous viral proteins (26). Efforts to extend these results to humans have been unpredictable.

CTLs that have been the subject of investigation in humans are usually generated from unseparated blood mononuclear cells and/or repeated stimulation of responding lymphocytes with exogenous IL-2 and viral antigens (4,5, 13,14,17–22). For example, Biddison et al (17) used repeatedly stimulated human blood cells in their elegant mapping studies of influenza peptides that are presented to CTLs. An efficient and effective system to generate human antigen specific cyntoxic T cells in general, and in particular influenza specific killer cells needs to be identified, especially one that capitalizes on the efficient accessory function of dendritic cells.

The use of dendritic cells to process and present antigens is described in Steinman application PCT/US92/. Accordingly, it would be useful to provide additional means of delivering various antigens to specific populations of dendritic cells. Such delivery systems could be useful for providing an efficient and effective system to generate human antigen specific cytotoxic T cells in general and, in particular, influenza specific killer cells.

Influenza A virus infection remains a major cause of mortality and morbidity, primarily because the control of the respiratory-illness has not been achieved through vaccination. Current vaccines are designed to. boost antibody responses to viral antigens [HA and NA] that undergo antigenic drift and shift (10). Consequently, the protective effects of antibodies decline with time. Vaccines directed towards the induction of influenza virus-specific cytotoxic T cell immune responses might be far more effective, since CTL have been shown to express cross reactivity in recognition of subtypes of influenza A (18). There is evidence in humans that CTL responses play a role in recovery from infection. McMichael et al (13) related levels of CTL immunity to clearance of nasal virus by normal donors inoculated with live virus. A clear association was observed between CTL responses and clearance of virus.

An ideal vaccine would utilize cross-reactive antigens, induce CD8+ CTL responses in most hosts, and have an efficient means of delivery. Several approaches to induce CTLs with these properties have been attempted in a number of systems. They include delivery of Class I-restricted peptides with adjuvant (58–61), conjugated to lipid (62), complexed with immune stimulating complexes (ISCOMs) (63), or inserted into liposomes (64,65). The injection of DNA encoding the immunizing antigen directly into skeletal muscle (66) has also been reported to induce CTL.

Until recently, dendritic cells have not been directly considered in strategies to design new vaccines that generate CD8+ CTLs. Targeting antigen to dendritic cells has several advantages; one can maximize the efficiency of T cell activation (9), and avoid anergy induction (67) or the use of adjuvants (68). For example, dendritic cells pulsed with antigen in vitro and delivered in vivo to mice have been highly effective for generating CD4+ immne responses to protein antigens and microbes (68,69). Mouse dendritic cells pulsed with Class I restricted peptides of NP (26), HIV peptides (70), or given antigen via pH sensitive liposomes (65) into the cytoplasm can induce CTL responses.

SUMMARY OF THE INVENTION

This invention relates to the presentation of antigens in the immune system. More specifically, this invention relates to the use of viral vectors to deliver antigens to dendritic cells for processing and presentation to T cells. Delivery of antigens to dendritic cells have preventive, diagnostic and therapeutic applications.

In one embodiment, this invention relates to a method of delivering antigens to dendritic cells comprising providing a viral vector comprising a gene sequence encoding for the antigen and exposing the dendritic cells to the viral vector for a time sufficient to allow the antigen to be expressed on the surface of the dendritic cells. The viral vector, in a preferred embodiment is an influenza virus.

In another embodiment of this invention, the viral vector comprises nucleic acid prepared by recombinant techniques so as to encode antigens which are not encoded by the native viral vector. upon infection of dendritic cells, expression of the nucleic acid results in the synthesis of protein antigens including those which are not native to the virus. The antigens are then processed and presented on the MHC I antigens of the dendritic cells which, according to one embodiment of the invention, may then be used to activate T cells, such as, for example, cytotoxic T lymphocytes.

Accordingly, this invention also provides a method of generating antigen specific cytotoxic T lymphocytes. This method comprises providing a viral vector comprising a nucleic acid sequence encoding the antigen and exposing at least one dendritic cell to the vector for a time sufficient to allow the antigen to be processed and expressed on the surface of the dendritic cell. The dendritic cells are then exposed to T lymphocytes for a time sufficient to cause their activation to antigen specific cytotoxic T lymphocytes.

Various types of antigens are suitable for delivery by the viral vectors. In particular, such antigens include, but are not limited to, tumor antigens, viral antigens, bacterial antigens, protozoans, and autoimmune antigens.

In another embodiment of the invention viral activated dendritic cells are used to activate T cells in vitro as a method of assaying the responsiveness of T cells to antigens.

Methods of preventing, and treating disease are also provided by this invention which comprise administering to an individual in need of treatment, a therapeutically effective amount of cytotoxic T cells which have been activated by viral activated dendritic cells.

In addition to the methods of this invention, this invention also provides virally activated dendritic cells, and in particular human activated dendritic cells which are prepared according to the methods of this invention. Cytotoxic T lymphocytes which have been activated by the dendritic cells of this invention are another embodiment of this invention.

It is a general object of this invention to provide a method of using viral vectors efficiently to deliver specific antigens to dendritic cells which are then expressed on their surface.

It is another object of this invention to provide a method of using influenza viral vectors to deliver specific antigen to dendritic cells which are then expressed on the surface of the dendritic cells.

It is yet a further object of this invention to generate antigen specific cytotoxic T lymphocytes either in vitro or in vivo by using the dendritic cells generated by the methods described herein.

It is yet another object of this invention to provide a method of prophylactic or therapeutic immunization for a variety of cancers, autoimmune diseases or pathogens using the dendritic cells described herein.

In addition, it is another object of this invention to provide multivalent vaccines that can be used either prophylactically or therapeutically for immunization using the dendritic cells generated by the methods described herein.

DESCRIPTION OF FIGURES

FIGS. 1A–E show dendritic cells which were pulsed with virus for 60 min, washed extensively and then cultured for 16 h. FIG. 1F shows dendritic cells cultured for 1$h$ following the virus pulse. FIGS. 1G and 1H show purified monocytes infected with influenza as above and cultured for 16 h. At the end of the culture period, cells were collected, cytospins were prepared and stained with the following panel of monoclonal antibodies (mAbs). B B [9.3C9, anti-ClassII].

(1A) Control mAb [OKT8]. Black arrows depict contaminating CD8+ T cells in the APC population. A white arrow illustrates a negatively stained dendritic cell.

(1B) Control mAb [9.3C9. anti-Class II]. The three headed arrow identifies typical dendritic cells.

(1C) Anti-NP [HB65]. The black arrow points to the intense nuclear location of NP in a dendritic cell.

(1D) Anti-HA [H17L2]. The arrow points to a typical dendritic cell.

(1E) Anti-HA [H28E231]. The arrow point to a typical dendritic cell.

(1F) A 1 hour infection of dendritic cells.

(1G) Overnight infection of monocytes stained with anti-HA [H28E23].

(1H) Anti-NP [HB65]. NP is detected in several dying and live monocytes.

Figure 1A:
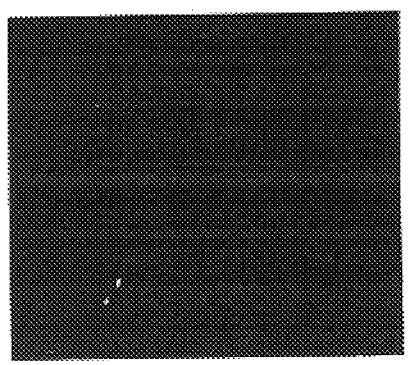
FIGS. 1A–H are photomicrographs which show that following infection with influenza virus, dendritic cells express hemagglutinin (HA) and nucleoprotein (NP) proteins.
Figure 1B:
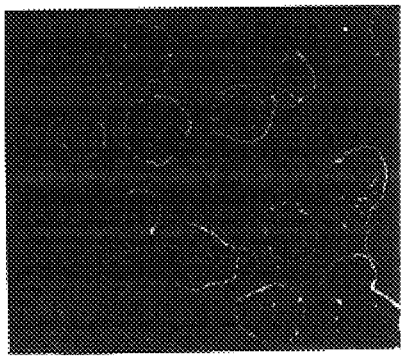
Figure 1C:
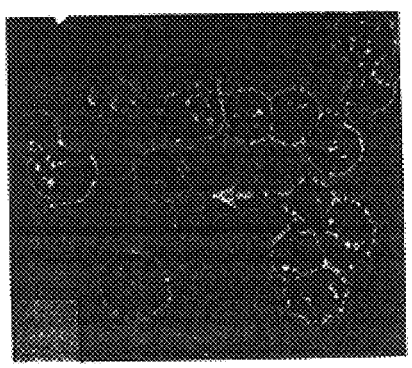
Figure 1D:
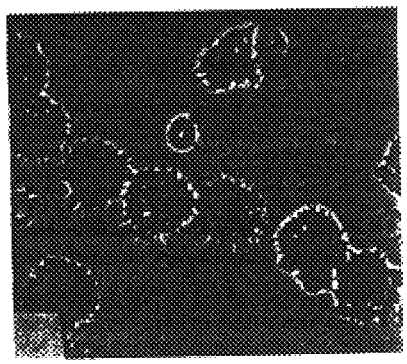
Figure 1E:
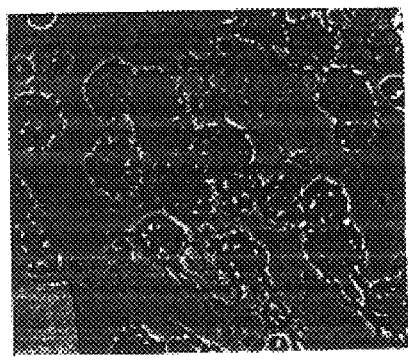
Figure 1F:
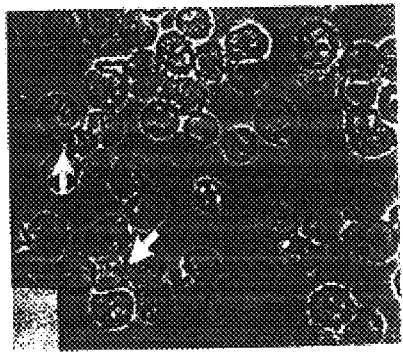
Figure 1G:
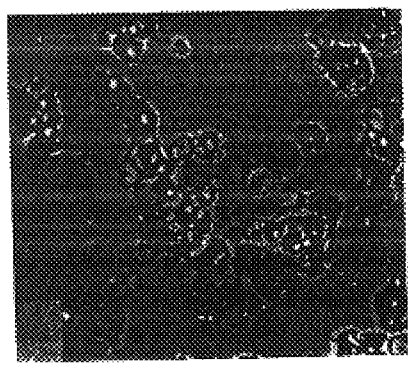
Figure 1H:
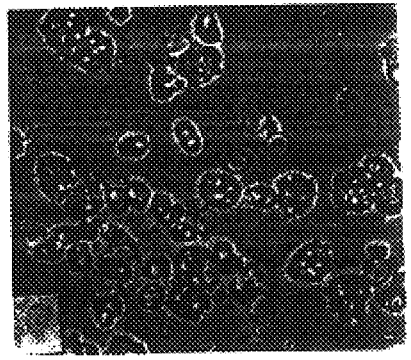

In FIG. 1E, the arrows identify typical dendritic cells, with hairy processes as expected for a plasma membrane envelope protein. In FIG. 1F, white arrows point to the granular appearance of HA presumably in endosomal granules, black arrows point to the diffuse location of HA-in a few rapidly infected dendritic cells. In FIG. 1G, dying infected monocytes are phagocytosed by non-infected cells [black arrow].

Figure 2:
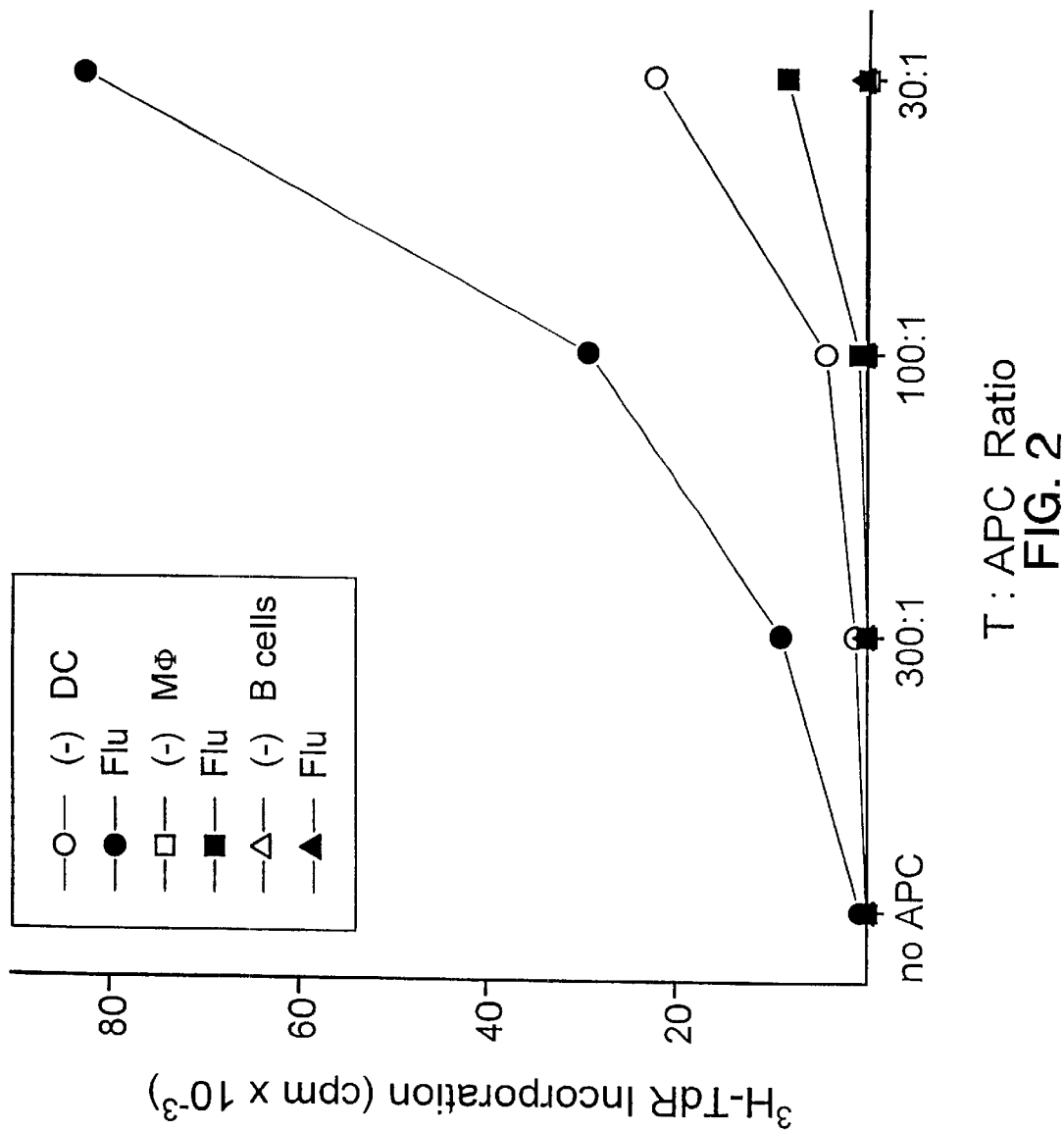

FIG. 2 shows influenza virus-infected dendritic cells stimulate T cell proliferative responses. Bulk T cells were tested in a standard proliferation assay for responsiveness to influenza virus-infected and noninfected dendritic cells, macrophages and B cells at various T:antigen presenting cell (APC) ratio ratios. Cultures were pulsed on day 5 for 9 h with 4 uCi/ml of $^3$H-TdR. Results are means of triplicates.

Figure 3B:
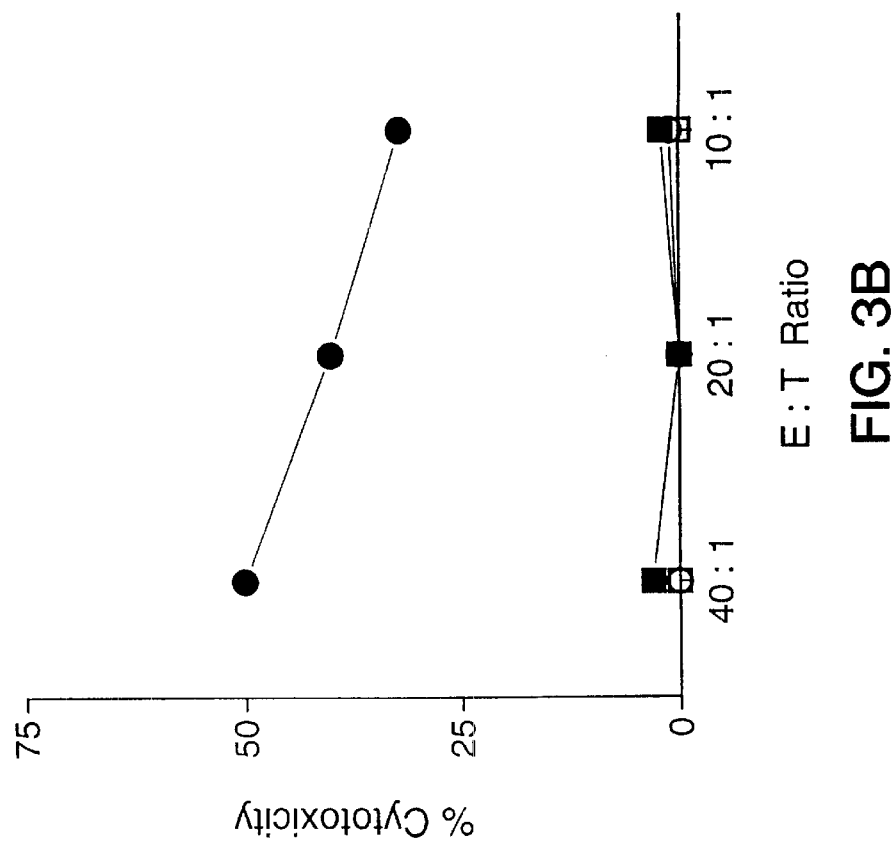
Figure 3A:
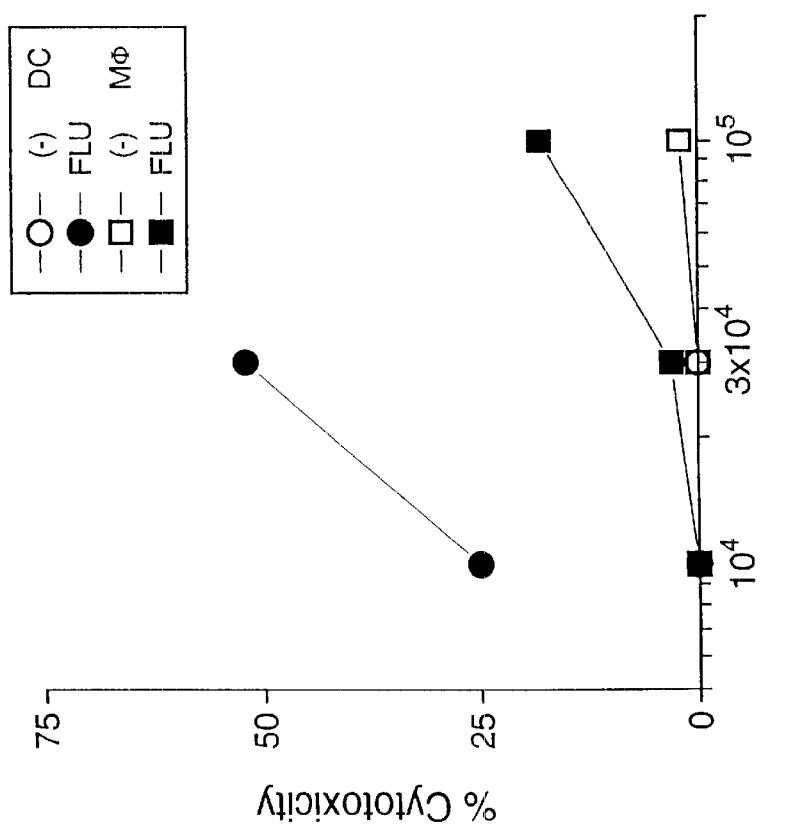

FIGS. 3A–B show dendritic cells are potent stimulators for the induction of influenza specific CTL responses.

(3A) $1 \times 10^6$ purified T cells from buffy coat donors were stimulated with graded doses of uninfected [open symbols] or influenza virus-infected [closed symbols] dendritic cells or monocytes. After 7 days, CTL activity was measured using infected syngeneic monocytes as targets at ratio of 40:1. Lysis of uninfected target cells was <5% at all doses of stimulators used.

(3B) Purified T cells were cultured with uninfected or infected dendritic cells or monocytes at T:APC ratios of 30:1 for 7 days. Lytic activity was measured on syngeneic monocyte targets at various E:T ratios, as shown. Lysis of uninfected target cells was <5% at all E:T ratios used.

Figure 4:
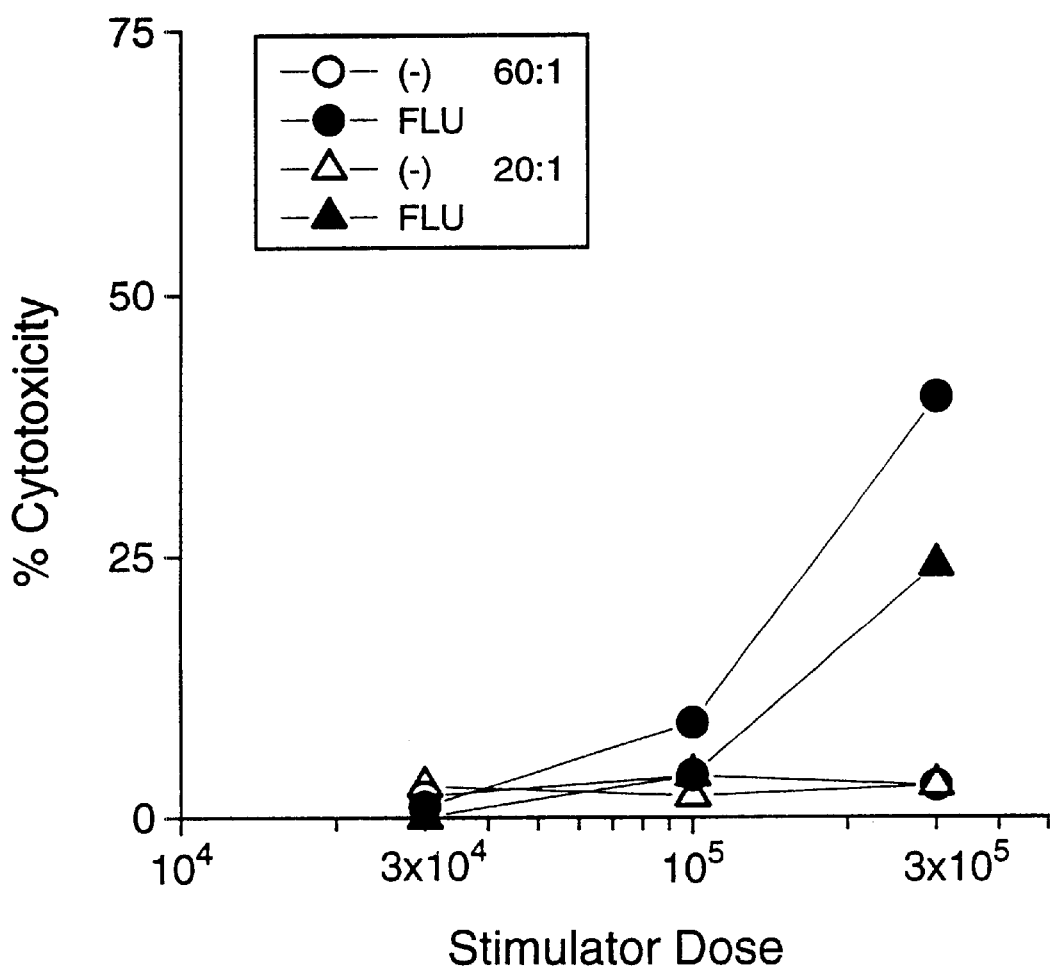

FIG. 4 shows partially enriched preparations of dendritic cells suffice as stimulators of influenza specific CTL responses. $1 \times 10^6$ purified T cells were cultured with graded doses of uninfected [open symbols] or infected ER-,FcR- cells comprising approximately 5% dendritic cells [closed symbols]. Lytic activity was measured on syngeneic targets on day 7 of culture at E:T ratios of 60:1 and 20:1. Lysis of uninfected target-cells was 5% at all stimulator doses and E:T ratios used.

Figure 5:
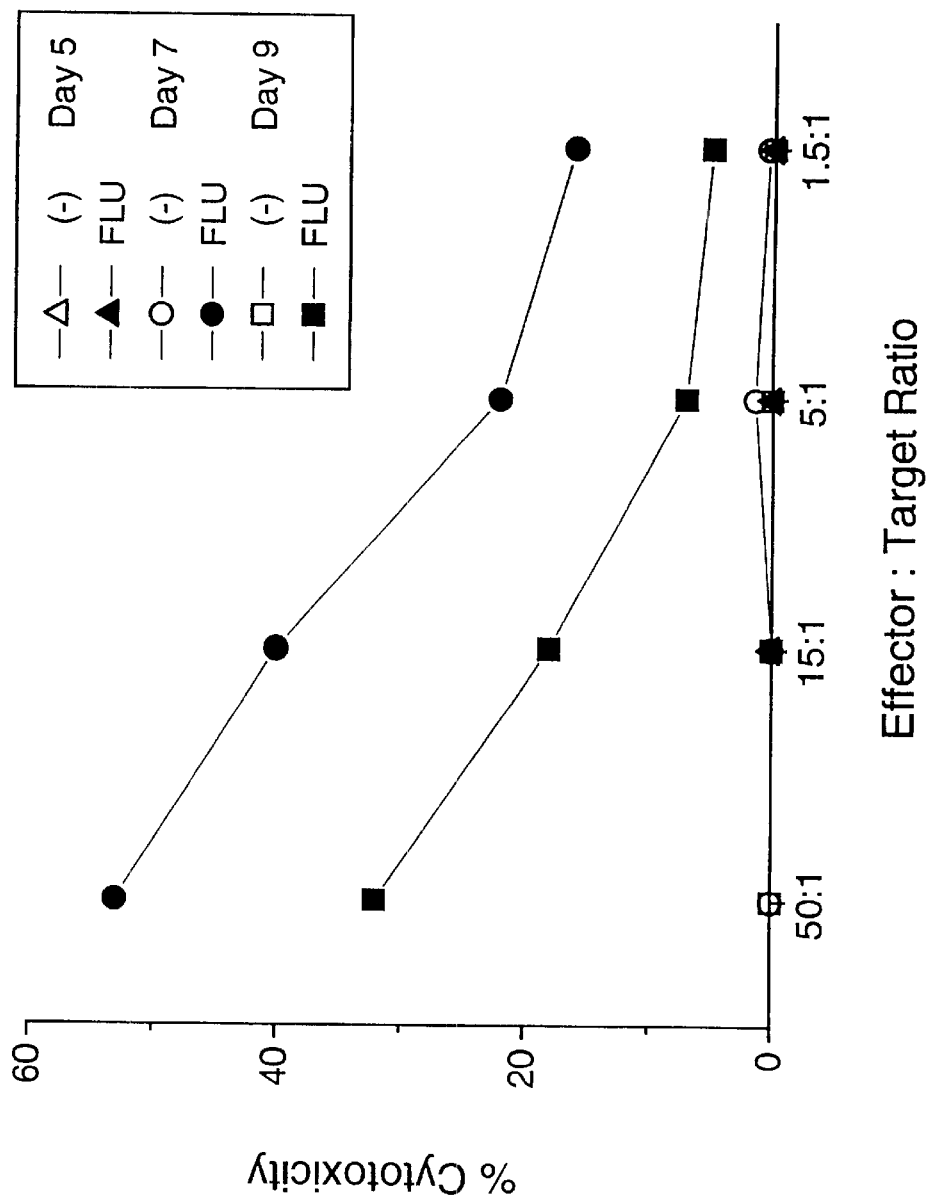

FIG. 5 shows kinetics of CTL development. Purified T cells obtained from a buffy coat donor were stimulated with partially enriched populations of uninfected [open symbols] or influenza virus-infected [closed symbols] dendritic cells at T:APC ratios of: 3:1. Lytic activity was measured at day 5, 7 or 9 on infected syngeneic monocyte targets. Lysis of uninfected monocyte targets was <5% at all time points assayed.

FIGS. 6A–F shows CD4/CD8 phenotype in bulk T cell populations responding to influenza virus antigens. Bulk T cells were cultured with uninfected or infected APCS for 7 days, after which they were phenotyped for CD4 or CD8 expression as described in Example.1. Dot plots are of forward versus side scatter [left panels], antiCD4-FITC versus forward scatter [middle panels] or anti-CD8-PE versus forward scatter [right panels]. Note that the majority of large cells responding to infected APCs are CD8+.

Figure 7B:
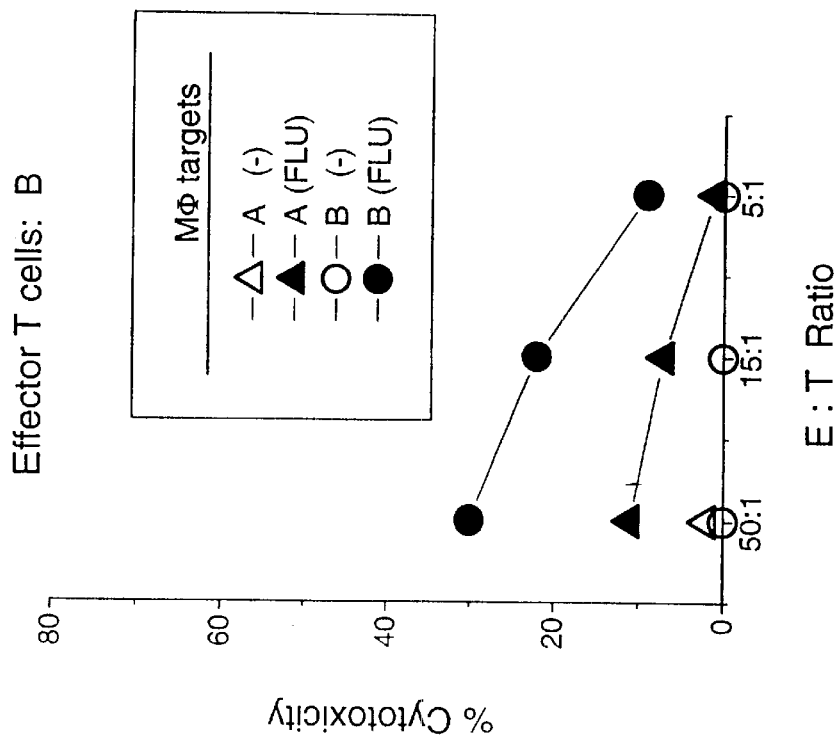
Figure 7A:
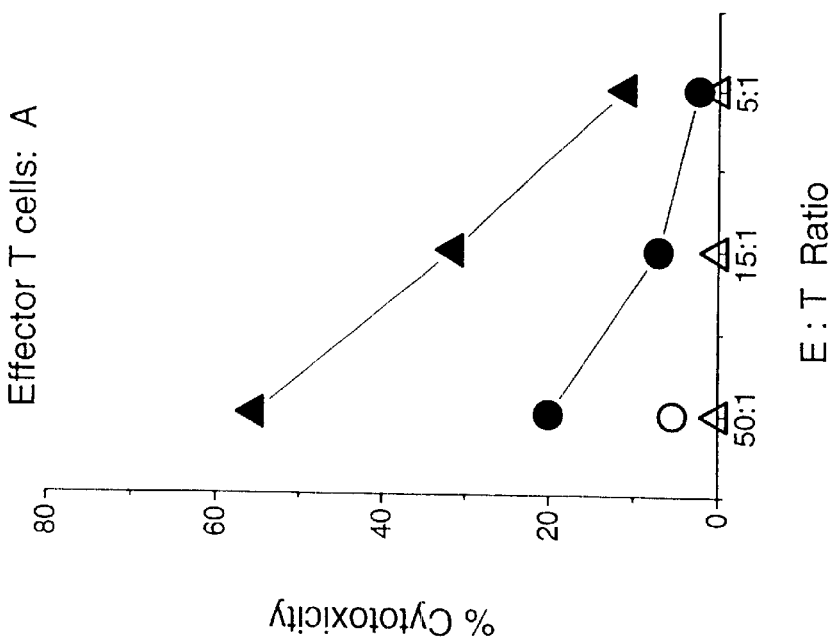

FIGS. 7A–B shows evidence that human influenza specific CTL are Class I restricted. Donors A and B, who differ at Class I but share Class II antigens [DRw52, DQwl], served as sources of T cells and APCs. T cells were cultured with infected or uninfected syngeneic APCs for 7 days after which the cells were harvested for CTL activity. Lytic activity was measured on syngeneic and allogeneic macrophage targets. Uninfected APCs failed to elicit CTL activity [data not shown].

Figure 8:
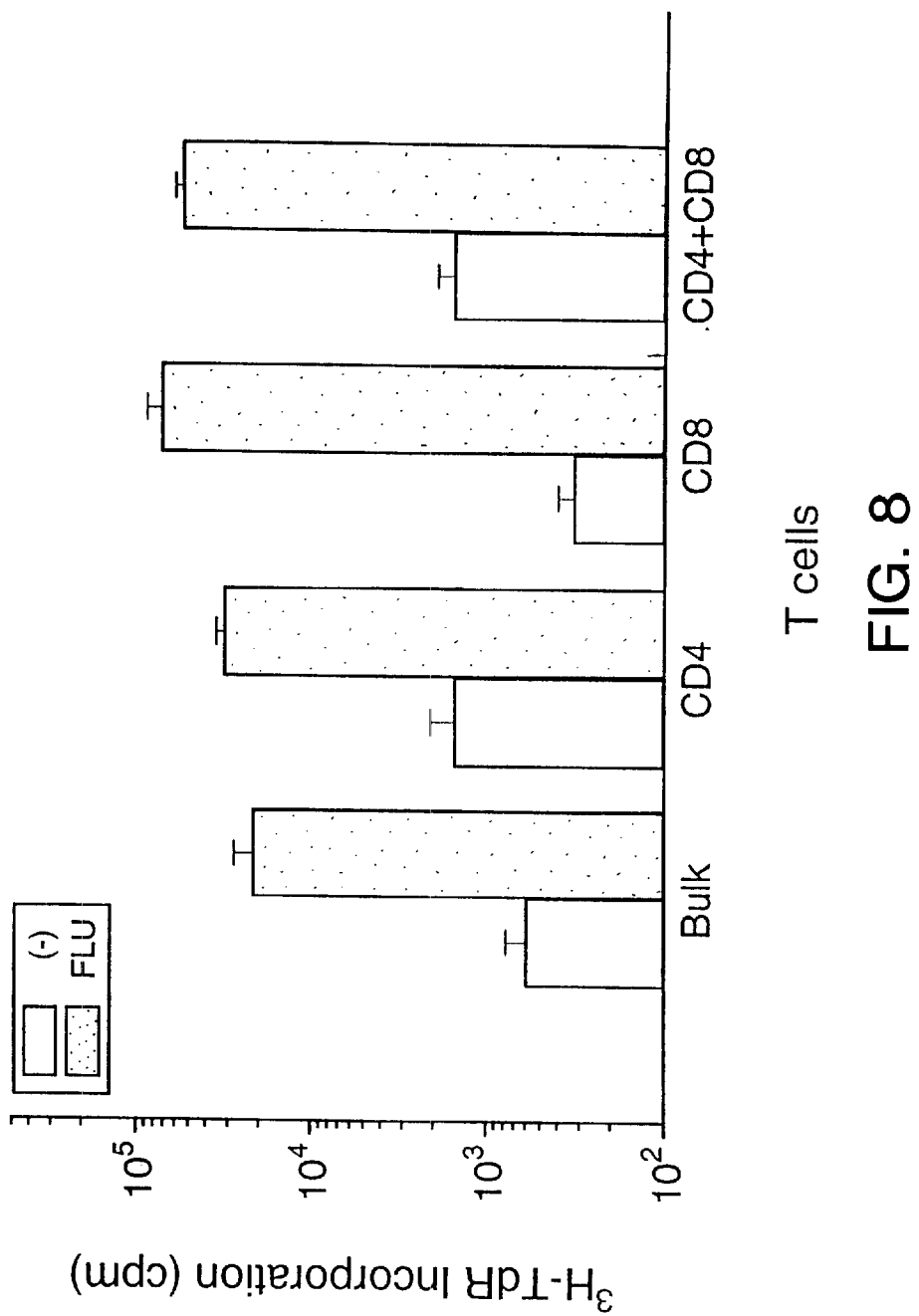

FIG. 8 shows purified CD4+ and CD8+ T cells proliferate to influenza virus-infected dendritic cells. CD4+ and CD8+ T cells were purified from a bulk T cell population to greater than 98% by staining with specific mAbs, followed by sorting on a Facstar plus, as described in Example 1. Bulk T cells, sorted CD4+, CD8+ and a combination of both sorted populations [CD4:CD8; 2:1] were tested in a standard proliferation assay for responsiveness to influenza virus-infected ER, FcR-cells. The T:APC ratio was 5:1. Clear bars represent the responses to uninfected APCs while shaded bars represent the influenza virus-specific responses. Cultures were pulsed on day 5 for 12 h with 4 uCi/ml of $^3$H-TDR. Results are means of triplicates +/- S.D. Note the log scale on the y axis.

FIGS. 9A–D shows dendritic cells stimulate the development of both CD4+ and CD8+ influenza virus-specific CTL. Bulk T cells, sorted purified CD4+ or CD8+ cells were stimulated with uninfected [open symbols] or infected [closed symbols] ER-,FcR- cells for 7 days. The T:APC ratio was 3:1. Cytolytic activity was measured on uninfected and infected syngeneic monocytes. CD4+ and CD8+ cells were also added together at a 2:1 ratio prior to the CTL assay [last panel on the right]. Lysis of uninfected monocyte targets was <5% at all E:T ratios tested.

Figure 10A:
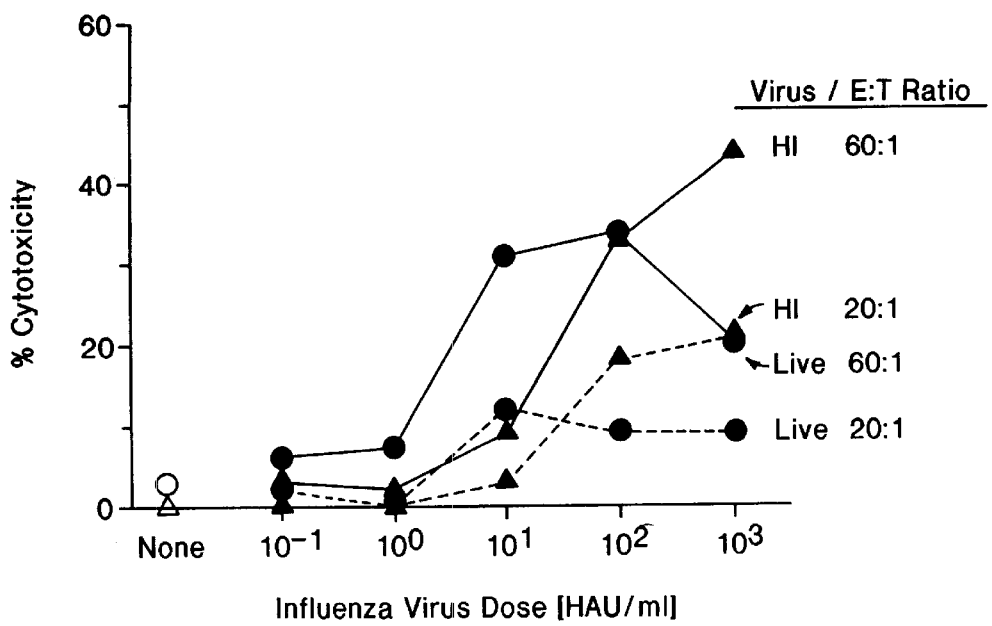
Figure 10B:
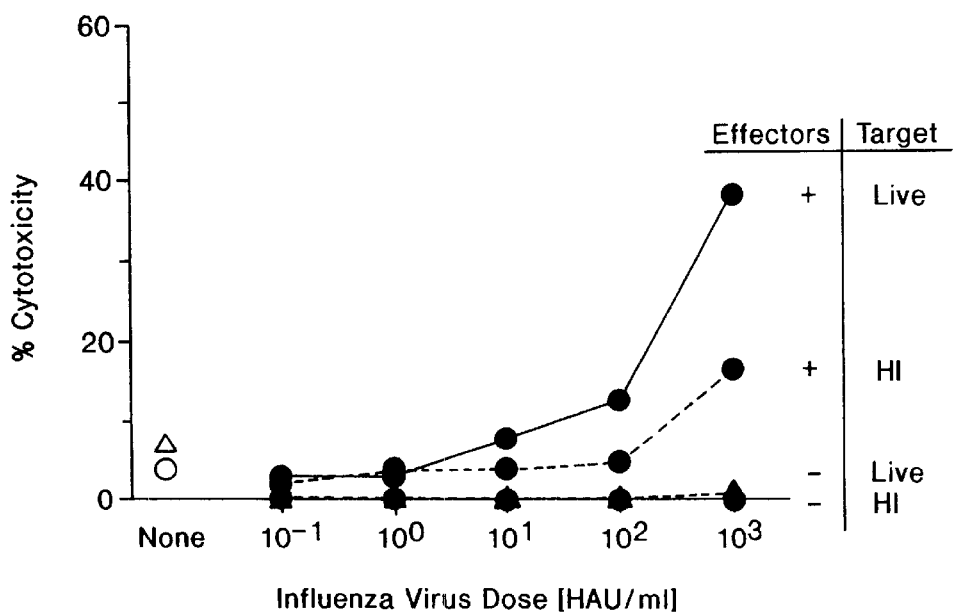

FIGS. 10A–B. FIG. 10A shows dose response titration of live versus heat inactivated virus. Partially enriched preparations of dendritic cells were pulsed for 1 hr at 37° with several dilutions of live or HI virus, in serum free medium. Cells were washed and then added to syngeneic donor T cells at 3:1 T:APC ratio. After 7 days, CTL activity was assayed as described in Table II. %CTL shown is on infected syngeneic monocytes targets at two E:T ratios. Lysis of uninfected targets was <5% at all E/T ratios used [data not shown]. FIG. 10B shows that heat inactivated virus poorly sensitizes target cells for CTL recognition. Influenza specific CTLs were generated from bulk cultures of T cells and partially purified dendritic cells that had been pushed with live influenza virus at 1000 HAU/ml. The CTLs were tested on syngeneic macrophage targets that were infected with live, or HI virus at dilutions of 10-1 to 103 HAU/ml. E:T ratio=60:1. Lysis of uninfected targets was <5% at all E/T ratios used [data not shown].

Figure 11C:
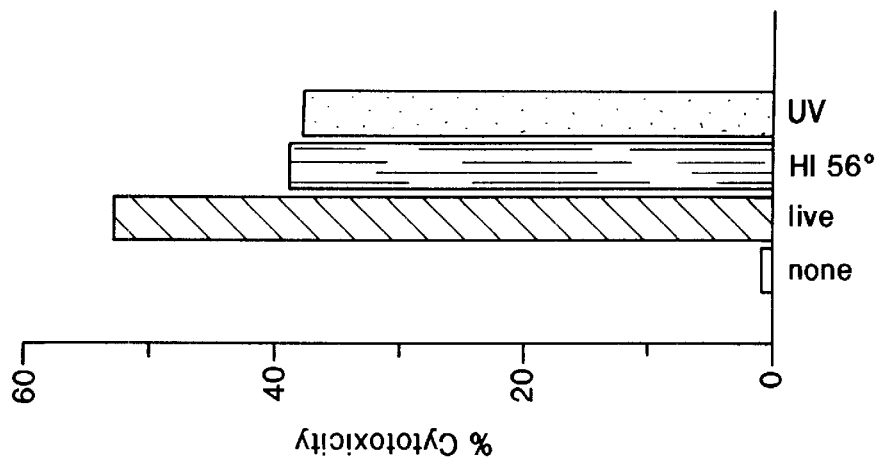
Figure 11B:
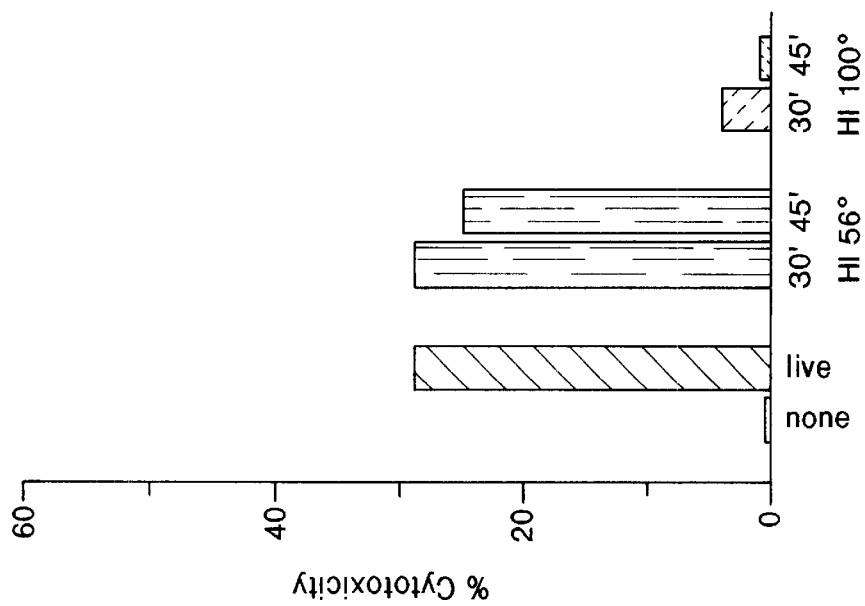
Figure 11A:
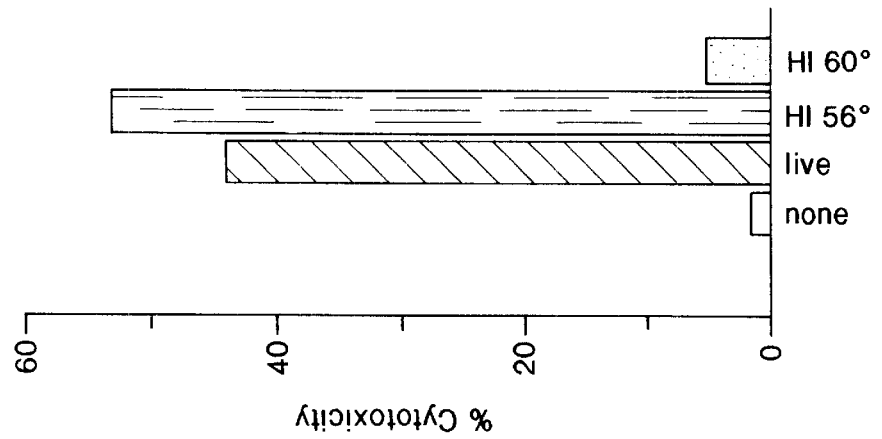

FIGS. 11A–11C shows induction of influenza virus-specific CTL with noninfectious virus. Partially purified dendritic cells pulsed with live, HI [56°, 60°, or 100° at 30–45 min] or UV inactivated virus, were cultured with syngeneic T cells for 7 days after which CTL activity was measured on macrophage targets. E=T ratios are 40:1 [FIG. 11A]; 50:1 [FIG. 11B]; 60:1 [FIG. 11C]. Lysis of uninfected targets was <5% at all E/T ratios used [data not shown].

Figure 12A:
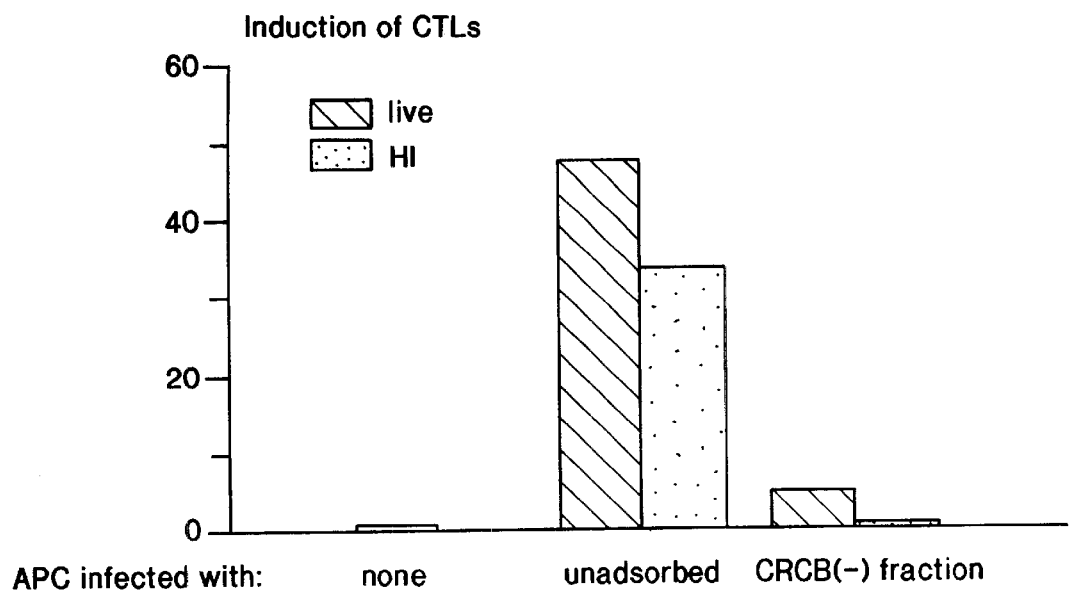
Figure 12B:
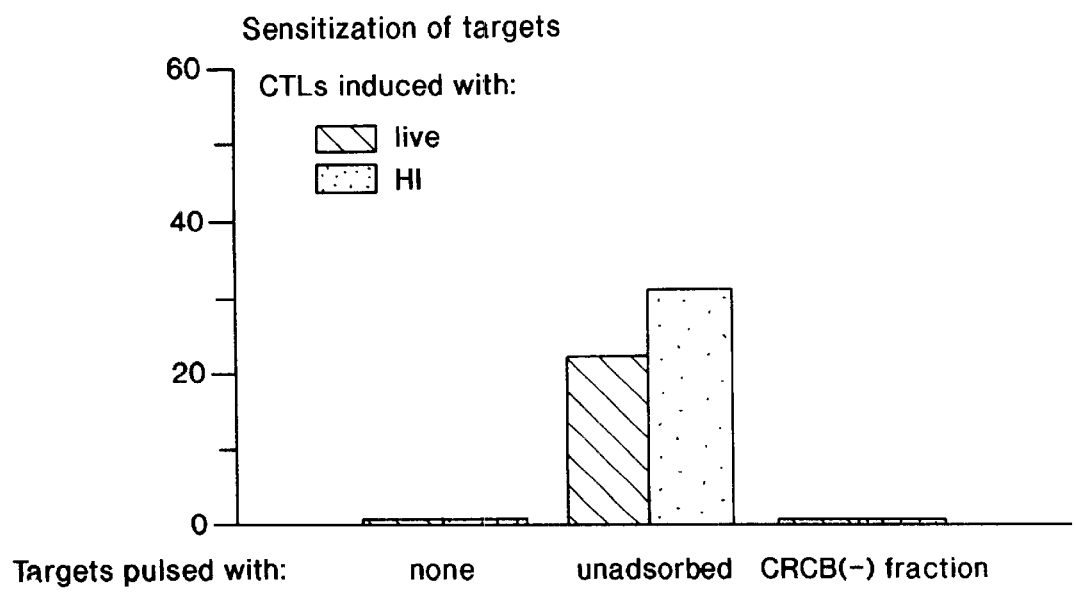

FIGS. 12A–12B. FIG. 12A shows adsorption of virus with CRBC removes CTL inducing activity, partially enriched preparations of dendritic cells were pulsed with live or HI influenza virus before or after adsorption of CRBC. We used the known hemagglutinating property of influenza viruses to adsorb and remove virions from chicken embryo allantoic fluids containing virus. Washed chicken red blood cells (CRBC) were resuspended to 20% v/v in RPMI and were gently mixed with an equal amount of allantoic fluid. After 20 min of incubation on ice, cells and bound virus were spun down at "low speed" (1000 rpm, 5 min. 4° C.). Supernatants were taken for 2 more cycles of incubation with CRBC as above. The final supernatant was spun down twice and considered to be a 1:8 dilution of the starting virus preparation. Partially enriched preparations of dendritic cells were pulsed with live or HI influenza virus before or after adsorption to CRBC [CRBC-fraction] and tested for their ability to stimulate CTL responses. %CTL activity is shown on infected macrophage targets. Lysis of uninfected targets was <5% at all E/T ratios used [data not shown]. FIG. 12B shows adsorption of virus with CRBC prevents sensitization of macrophage targets. CTLs induced with live or HI virus were tested on macrophage targets that had been infected with live unabsorbed virus or the adsorbed nonbound fraction [CRBC-], at 1000 HAU/ml. %CTL activity is also shown on uninfected targets.

Figure 13:
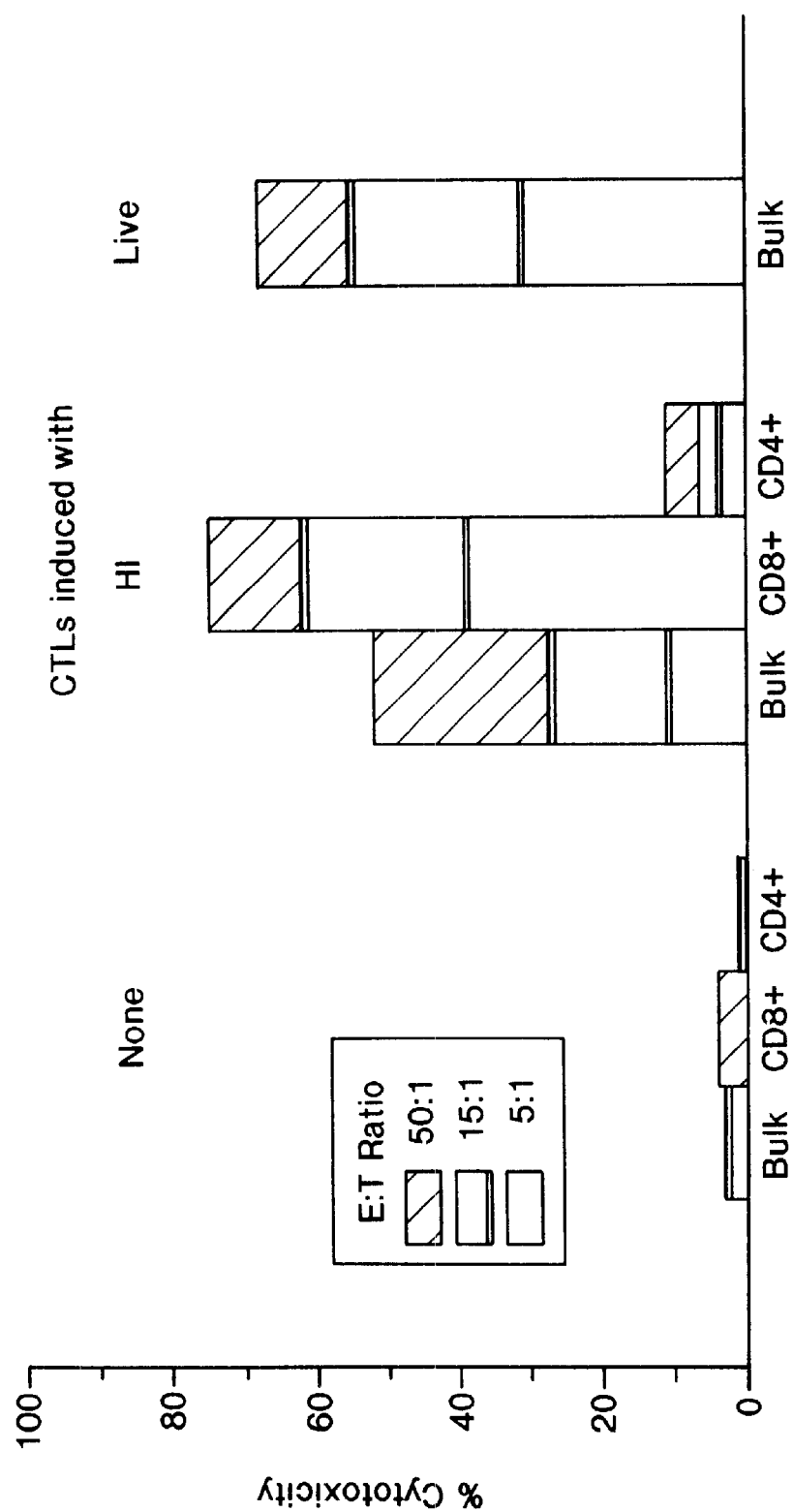

FIG. 13 shows influenza-virus specific CTLs generated to HI virus are CD8+. Purified T cells were stimulated with partially enriched populations of uninfected, live influenza virus infected or HI influenza virus infected dendritic cells at T:APC ratios of 3:1. After 7 days of culture, T cells stimulated with uninfected or HI influenza-infected APCs were stained with CD4-FITC and CD8-PE mAbs and sorted on a FACStar Plus. The CD4+ and CD8+ populations were >98% pure. Lytic activity of each population was measured on infected syngeneic macrophage targets. Data is representative of three experiments. Lysis of uninfected targets was <5% at all E/T ratios used [data not shown].

Figure 14:
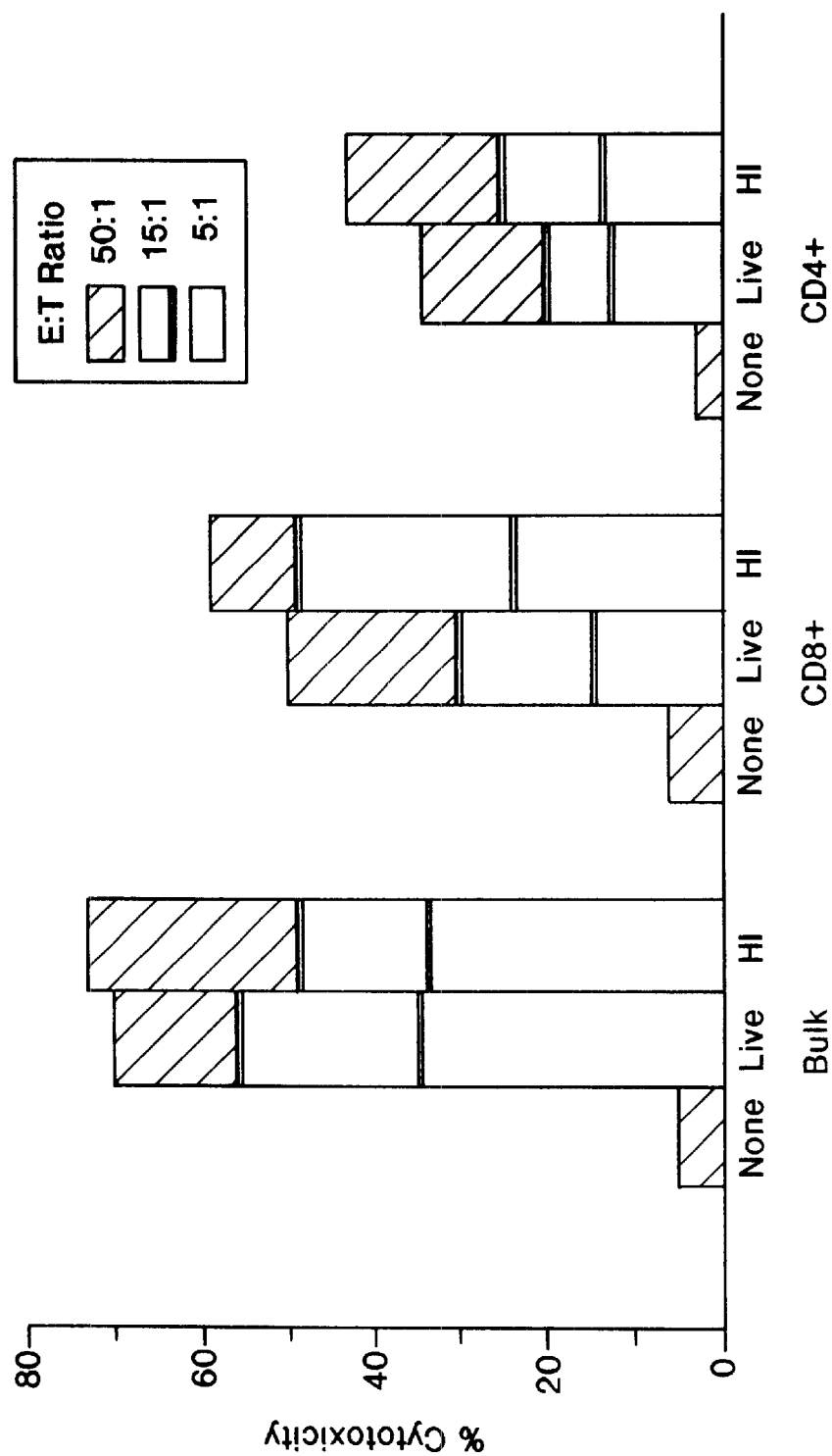

FIG. 14 shows that live and HI influenza virus stimulate the development of both CD4+ and CD8+ CTLs. T cells were further purified into CD4+ or CD8+ subsets by staining with Leu2 or Leu3 mAbs, followed by panning onto plastic plates coated with goat anti-mouse IgG. Cells depleted by panning constituted <3.5% of the resulting subpopulation as monitored by cytofluorography. Bulk and purified T cell subsets were stimulated with partially purified dendritic cells that were uninfected or infected with live or HI virus for 7 days. The T:APC ratio was 3:1. Cytolytic activity was measured on uninfected and infected syngeneic macrophages. Lysis of uninfected targets was <5% at all E/T ratios used [data not shown].

DETAILED DESCRIPTION OF THE INVENTION

For the purpose of a more complete understanding of the invention, the following definitions are described herein:

By antigen or immunogen we mean all or parts thereof of a protein or peptide capable of causing a cellular or humoral immune response in a mammal. Such antigens are also reactive with antibodies from animals immunized with said protein. Examples of antigens that can be used in this invention include, but are not limited to, viral, bacterial, protozoan, microbial and tumor antigens. Preferred antigens include influenza virus, malaria, HIV, and melanoma antigens.

Mammal includes but is not limited to humans, monkeys, dogs, cats, mice, rats, pigs, cow, horses, sheeps and goats.

For the purposes of this invention, by viral vector means a vector that comprises all or parts thereof of a viral genome which is capable of being introduced into dendritic cells and expressed. Such viral vectors may include native, mutant or recombinant viruses. Such viruses may be RNA or DNA viruses. Examples of suitable viral vectors include adenovirus, HSV, vaccinia, vesicular stomatitis virus (VSV) and influenza. Preferably, the virus is an influenza virus.

Influenza viral vector means a vector comprising all or parts thereof of an influenza viral genome. Intended to be included in this definition are Influenza A, B, C and strains and subtypes thereof. In a preferred embodiment the influenza virus is PR8.

The human dendritic cells which may be used to practice this invention preferably may be obtained as mature dendritic cells from an appropriate tissue such as blood or bone marrow as described herein or by methods known in the art. Proliferating cultures of dendritic cell precursors may be obtained as described in Steinman et al. WO 93/208185 and as described in Romani et al (1994) *J. Exp. Med.* Vol. 180:83 to 93, all of which are incorporated herein by reference. Viral vectors including influenza vectors, can be used to deliver antigen to either proliferating or mature dendritic cells either freshly isolated or obtained from in vitro culture.

To deliver antigens to dendritic cells for. presentation to cells of the immune system, specifically T cells. In accordance with this invention antigens are introduced to dendritic cells via a viral vector comprising a nucleic acid sequence encoding for an antigen. The viral vectors useful for practicing the method of this invention should be capable of entering dendritic cells and localizing to the cytoplasm. Such viral vectors are endocytosed by the dendritic cells and pass through the endocytic membrane and are ultimately processed by the dendritic cells for presentation of antigens on MHC Class I receptors located on the dendritic cell surface.

Examples of such viral vectors include those stated above, and in particular, but are not limited to influenza virus, vascular stomatitis virus and vaccinia virus. Preferred vectors are influenza virus. Most preferred is influenza.

Examples of influenza viruses that can be used to construct all or part of the vectors include, but are not limited to Influenza A, Influenza B, Influenza C, and strains and subtypes thereof. In a preferred embodiment, the influenza A virus, PR8, well-known to workers in the field (*Virology* 2nd Edition (1990) eds. B. A. Fields and D. M. Knipe, Raven Press, N.Y.) is used to deliver influenza, modified influenza or non-influenza antigens to dendritic cells. The influenza virus may be used to infect dendritic cells in its native or natural form without modification.

Other suitable vectors for use with this invention may be identified by assaying for a viral vector's ability to enter dendritic cells to synthesize viral protein in the case of replicating virus, and to lead to antigen presentation in the case of replicating and non replicating virus.

In another embodiment of this invention, vectors may be targeted to dendritic cells by modifying the viral vector to encode for a protein or parts thereof that is recognized by a receptor on dendritic cells, whereby occupation of the dendritic cell receptor by the vector will initiate endocytosis of the vector allowing for processing and presentation of antigens encoded by the nucleic acids of the viral vector. The nucleic acids which is delivered by the virus may be native to the virus which when expressed on the dendritic cell encodes viral proteins which are then processed and presented on the MHC receptor of the dendritic cell. Alternatively, the-native nucleic acid may be modified using recombinant techniques to include nucleic acid sequences encoding amino acid. sequences which define antigens which are not native to the infecting virus. Construction and modification of viral vectors is performed by conventional molecular or genetic manipulation (Sambrook et al (eds)

(1989). In "Molecular Cloning—A Laboratory Manual" Cold Spring Harbor Press, Plainview, N.Y. and Ausebei et al. (eds) in "Current Protocols in Molecular Biology" (1987) John Wiley an Sons New York, N.Y.).

As with other viral vectors, construction and the use of influenza viral has been reported in the art (Li et al. (1992)) *Journal of Virology* 66(1):394–404; Li et al. (1993); *Proc. Natl. Acad. Sciences* (USA) 90:5214–5218) which are incorporated herein by reference.

In one embodiment of this invention a viral vector is comprised of the native viral genome. As discussed above, in other embodiments mutant viral strains or recombinantly modified viral strains are also suitable for use with this invention.

Influenza viral vectors may be used to provide influenza antigens to the dendritic cells that may cross react with other types, subtypes or strains of influenza virus. Alternatively, the dendritic cells may express type, subtype, or strain specific antigens.

In one embodiment, influenza virus may be modified to deliver antigens for other types, subtypes or strains of influenza thereby providing immunizing against a broad spectrum of influenza virus. It is known on the art that cross reactive viral epitopes are presented on Class I molecules.

Examples of noninfluenza antigens, include, but are not limited to tumor antigens, bacterial antigens, protozoan antigens, such as the malarial circumsporozite protein, microbial antigens, viral antigens, autoantigens, lesteriosis and any other antigens for which it is desired that they presented by dendritic cells. Examples of specific antigens include, but are not limited to MAGE-1 (Boone, et al. *Ann. Rev. Immuno.* 12:337–365 (1994), and the HIV gag protein.

To prepare the influenza vectors of this invention it should be recognized that the influenza virus is a negative strand RNA virus (*Virology*, 2nd Edition (1991) eds. B. N. Fields and P. M. Knipe et al.; Raven Press, New York). Construction and modification of influenza viral vectors carrying foreign antigens is known to those in the art (Luytjes; W. et al. (1989); *Cell* 59:1107–1113; Enami et al. (1990); *Proc. Natl. Acad. Sciences* (USA) 87:3802–3805; Enami et al. (1991); *J. Virology* 65:2711–2713; Muster, T. et al. (1991); *Proc. Natl. Acad. Sciences* (USA) 88:5177–5181). Influenza virus is a negative strand RNA virus, therefore modification of the viral genome requires conversion to a cDNA form and a ribonucleoprotein transfection methods known to workers in the field. Restriction endonuclease sites can be introduced into the viral cDNA by conventional methods allowing for insertion of nucleic acid sequences encoding antigens at the restriction endonuclease site. Preferably the endonuclease restriction site is unique to the viral vector. Examples of how to introduce restriction endonuclease sites include but is not limited to, mutagenesis. Alternatively, a sequence encoding an antigen can be inserted into the influenza viral vectors by homologous recombination. It is preferable that the sequence encoding the antigen be inserted into the hemagglutinins gene of the influenza viral vector so the antigen is expressed on the surface of the viral particle when formed. The nucleic acid sequence to be inserted may correspond to the entire peptide in which the antigenic region is contained or may correspond to the nucleic acid sequence encoding the exact antigenic epitope itself. Potential Class I antigens can be determined by one skilled in the art.

An influenza viral vector containing hemagglutinine epitopes from different subtypes of influenza A viruses can be constructed by using a ribonucleoprotein transfection method. (Li, S. et al. (1992) *J. of Virology*, 66:399–404). In this construct, the amino acid loop contained at antigenic site B in the A/WSN/33 (H1N1) (WSN) influenza virus was replaced by the corresponding structures of influenza virus A/Japan/57 (H2N2) and A/Hong Kong/868 (H3N2) (HK). This construct can be exposed to dendritic cells and the dendritic cells may take up this construct and thereby express epitopes of different subtypes of hemagglutins on their surface.

Alternatively, a construct expressing non-influenza epitopes can also be constructed. For example, a recombinant influenza virus expressing an epitope from the pathogen causing malaria, specifically, cytotoxic T-lymphocyte epitope can be genetically engineered into the hemagglutin in gene of an influenza viral construct. The influenza viral vector carrying the antigenic epitope for the cytotoxic T-lymphocyte epitope of the malaria parasite can then be exposed to dendritic cells allowing the dendritic cells to take up the viral vector and express the antigens on its surface.

Both replicating influenza viral vectors and non-replicating influenza viral vectors can be used in these methods. Influenza viral vectors can be made non-replicating by methods known to those skilled in the art. Examples of how to cause the viral vector to become non-replicating include, but are not limited to, heat inactivation or UV exposure. Non-replicating viral vectors are preferred for use in mammals. If a non-replicating viral vector is used the protein antigens desired to be expressed on the surface of the dendritic cell must be on or in the virus when it enters the dendritic cell. If a mechanism is available for the replicating virus to make protein in the dendritic cell then that would also be suitable. Otherwise, the proteins which are desired to be presented as antigens must be expressed on or by the virus prior to entry into the dendritic cells.

The dendritic cells used in this method can be isolated from human by conventional methods (see Example 1). Alternatively, the dendritic cells used in this method can be cultured in vitro by methods known to one skilled in the art and disclosed in PCT/US93/208185.

The ratio of influenza viral vector to dendritic cells that may be used are about 1 to 100 virus particle or vectors per cell. Other ranges may be determined based on the methods disclosed herein. The influenza viral vector should be exposed to the dendritic cells for a period sufficient for the dendritic cells to incorporate and process the viral vector or particle and express the antigens on the surface of the dendritic cells.

In yet another embodiment of this invention T-cells isolated from individuals can be exposed to the dendritic cells now expressing specific or selected antigen in vitro and then administered to a patient in need of such treatment in a therapeutically effective amount. Sources of T-lymphocytes can include, but are not limited to, peripheral blood, or lymph nodes. Such lymphocytes can be isolated from the individual to be treated or from a donor by methods known in the art and cultured in vitro. Viability is assessed by conventional methods such as trypan blue dye exclusion assay. Preferred ratios of dendritic cells to lymphocytes are about 1 dendritic cell to about 10 to 100 lymphocytes.

In yet another embodiment of this invention, the antigen specific dendritic cells or the antigen specific T-lymphocytes generated by methods described herein may be used for either a prophylactic or therapeutic purpose. When provided prophylactically, the dendritic cells or antigen specific T-lymphocytes are provided in advance of evidence or any symptom of the condition trying to be prevented. The prophylactic administration of the dendritic cells or T-lymphocytes serves to prevent or attenuate the conditions in a mammal. When provided therapeutically, the dendritic cells or T-lymphocytes are provided at, or shortly after the onset of the condition or the onset of any symptoms of the disease or condition trying to be prevented. The therapeutic administration of the dendritic cells or T-lymphocytes serves to attenuate the pathogenic condition or disease condition. In a preferred embodiment, dendritic cells infected with an influenzal viral vector such as PR8. Examples of how the dendritic cells expressing the selected antigen can be administered include, but is not limited to, intravenous, intraperitoneal or intralesional, or intranasal.

A pivotal role for dendritic cells in human disease prophylaxis and therapy is indicated by their ability to directly induce strong CD8+ CTL responses, as shown here for influenza virus. We would therefore expect that it would be possible to pulse dendritic cells directly with peptides or with attenuated virus for instance, and use these APCs in vivo to elicit CTL responses. By adapting the systems described herein, dendritic cells could also be used for generating large numbers of CD8+ CTL, for adoptive transfer to immunosuppressed individuals who are unable to mount normal immune responses. Immunotherapy with CD8+ CTL has been shown to amplify the immune response. Bone marrow transplant recipients given CMV specific CTL by adoptive transfer, do not develop disease or viremia (4). These novel approaches for vaccine design and prophylaxis should be applicable to several situations where CD8+ CTLs are believed to play a therapeutic role e.g. HIV infection (1-3), malaria (5) and malignancies such as melanoma (6,7).

Examples of diseases that may be treated by the methods disclosed herein include, but are not limited to bacterial infections, protozoan, such as malaria, lesteriosis, microbial infections, viral infections such as HIV or influenza, cancers or malignancies such as melanoma, autoimmune diseases such as psoriasis and ankolysing spondylitis.

Frequently, in clinical disease it is difficult to detect killer cells because of inadequate presentation. This invention also provides methods for assessing the cytoxic activity of T lymphocytes, and in particular the ability of cytotoxic T lymphocytes to be induced by antigen presenting dendritic cells to express cytotoxic activity. According to this method, a sample comprising T lymphocytes to be assayed for cytotoxic activity is obtained. Preferably, the cells are obtained from an individual from whom it is desirable to assess their capacity to provoke a cytotoxic T lymphocyte response. The T lymphocytes are then exposed to antigen presenting dendritic cells which have been caused to present antigen. Preferably, the dendritic cells have been infected with a viral vector, such as influenza, which has been modified to deliver a specific antigen. After an appropriate period of time, which may be determined by assessing the cytotoxic activity of a control population of T lymphocytes which are known to be capable of being induced to become cytotoxic cells, the T lymphocytes to be assessed are tested for cytotoxic activity in a standard cytotoxicity assay. Such assays may include the chromium release assay described herein.

The method of assessing cytotoxic T lymphocyte activity is particularly useful for evaluating an individual's capacity to generate a cytotoxic response against cells expressing tumor or viral antigens. Accordingly, this method may be useful for evaluating an individual's ability to defend against cancers, for example melanoma, or viruses. In addition, this method is useful to detect autoreactive killer cells and could monitor not only the presence of killer cells, but their response to therapy.

All books, articles, or patents reference herein are incorporated by reference. The following examples illustrate various aspects of the invention and in no way are intended to limit the scope thereof.

EXAMPLE 1

Use of Replicating Influenza Viral Vector to Deliver Antigen to Dendritic Cells

Materials & Methods

Culture medium. RPMI 1640 (Gibco Laboratories, Grand Island, N.Y.] supplemented with gentamicin [100 ug/ml], 5% human serum and 10 mM HEPES buffer.

Blood mononuclear cells. In most experiments, buffy coats served as sources of blood mononuclear cells [PBMCs] and were obtained from the New York Blood Center. Blood donors were also healthy volunteers who were HLA typed by conventional methods and selected for MHC Class I mismatch. PBMCs were separated into T cell-enriched [ER+] (erythrocyte rosette) and T cell-depleted fractions [ER−] as previously described (23).

T cells. ER+ cells were first depleted of monocytes by panning on dishes coated with human gamma globulin (24). MHC Class II+ and NK cells [CD16+ and CD11b+] were depleted by coating with mAbs 9.3C9 [ATCC;HB180], and 3G8 [gift of Dr. Jay Unkeless and OKM1 [ATCC;CRL 8026] respectively, followed by panning on petri dishes coated with goat anti-mouse IgG (8). The resulting T cell population contained fewer than 2–3% of contaminating MHC Class II+ and NK cells, as monitored by cytofluorography. In some experiments, T cells were enriched for CD4+ or CD8+ cells by incubation with Leu 2 or Leu 3 mAbs, respectively, followed by panning as above. CD4+ and CD8+ cells were >95% pure when evaluated by staining with PE- conjugated Leu 2 or Leu 3 [Becton Dickinson and Co. Mountainview, CA], both before and after the culture period that was used to generate influenza responses.

APC populations. Monocytes were obtained from ER-cells by adhering them onto plastic dishes for 60–90 min, and dislodged by pipetting. Nonadherent cells were subsequently used for purification of B cells and dendritic cells, as described previously (24,25). Residual monocytes were first removed by panning on gamma globulin coated plates (24). The ER−,FcR- cells proved to be adequately enriched in the dendritic cells that are needed as APCs for strong CTL responses. However, to further enrich the dendritic cells, and the potency of the APCs, ER-, FcR- cells were layered onto 14% metrizamide gradients (25). After sedimentation, dendritic cells localize to the low density interface, while B cells and NK cells are enriched in the high density interface. Dendritic cell purity was 50–70% with contaminants being B cells, NK cells and a few T cells.

Virus preparation. Influenza virus strain PR8 [A/Puerto Rico/8/1934] was kindly provided by Dr. Peter Palese [Mount Sinai School of Medicine, New York] in the form of infectious allantoic fluid. Virus was grown up and purified as previously described (26). Virus stocks were replenished from seed virus by Spafas Inc., Storrs CT and stored in liquid nitrogen (virus stock: 20,000 HAU/ml]. Virus titers were determined using a hemagglutination assay, as previously described (26).

Infection of cells. APCs and target cells were washed out of medium containing serum and resuspended in RPMI. at 0.5–1×10⁷ cells/ml. Virus was added at a final concentration of 1000 HAU (hemagglutininating units) PR8/ml and incubated for 60 min. at 37°. This dose is saturating for the induction of influenza-specific CTLs. To determine whether influenza infection proceeded through an acidic compartment in APCs, the cells were incubated in 10 mM NH$_4$Cl for 30 min. prior to adding virus and throughout the subsequent infection. In some cases, the NH$_4$Cl was added throughout the culture period, generally 24th.

Induction of influenza specific CTL. 1×10⁶ purified T cells were cultured in 24 well plates [Costar, Cambridge] with graded doses of influenza virus-infected or uninfected APCs, in a total volume of 1.1 ml. After 7 days of culture, the cells were harvested and distributed in varying numbers to 96 well microliter plates [100 ul per well]. CTL activity was measured using a $^{51}$Cr-release assay with infected or uninfected syngeneic monocytes as targets. 1×10⁴ targets in a volume of 50 ul were added to each well to generate Effecter:Target ratios ranging from 1:1 to 100:1.

$^{51}$Cr release assay—Monocytes were obtained from ER- cells by adhering them onto plastic dishes for 60–90 min, and dislodged by pipetting. 1×10⁷ monocytes were cultured in 10 ml volumes in 60 ml Teflon beakers [Savillex Corp., Minnetonka, Mn.] until use as targets in the CTL assay (27). For $^{51}$Cr labelling and infection, cells were collected on ice, washed free of serum and brought up to 1×10⁷/ml in RPMI. 400 uCi Na$^{51}$CrO$^4$ [1 mCi/ml sterile stock, New England Nuclear, Boston, Mass.] was added per 1×10⁷ monocytes. They were simultaneously infected with 1000 HAU PR8/ml HAU PR8 for 1 h at 37°. The targets were washed four times and resuspended at 2×10⁵ /ml, after which 50 ul was aliquoted to each well containing effector T cells. Spontaneous and total release samples were prepared by adding the targets to wells containing RPMI alone or 0.33% SDS, respectively. The plates were centrifuged for 2 min. at 15 g and incubated for 5h at 37° C. At the termination of the assay, the supernatant was collected with absorption cartridges using a harvesting press [Skatron Instruments Inc., Sterling Va.] and counted in a gamma counter. Percent specific $^{51}$Cr release was calculated from the following formula: 100 x [[Release by CTL-spontaneous release]/[Total release-spontaneous release]]. Spontaneous release was 15–25% of the total release.

FACS analysis of cell populations and cell sorting. In some experiments, T cells were separated into CD4+ and CD8+ subsets by sorting on a FACSTAR Plus™ [Becton Dickinson]. 1×10⁷ cells were stained with 20 ul of Simultest CD4-FITC/CD8-PE [Becton Dickinson] for 45 min. at 4° C., washed three times and sorted. CD4+ cells were collected as FITC+ cells while CD8+ cells were PE+.

Contamination of CD4+ cells with CD8+ cells or vice:versa, was <1%. Sorted populations were stained again following a period of 7 days and did not demonstrate any change in their CD4/CD8 phenotype.

Detection of influenza virus infection by immunohistochemistry. Cytospins of various cell populations were prepared using a Shandon Cytospin 2 Centrifuge. Slides were fixed in acetone for 5 min at room temperature, and then incubated in hybridoma supernatant for 45 min. The mAbs to influenza virus proteins were kindly provided by Dr. J. Yewdell, NIH, and included anti-NP [H16-L10-4R5; ATCC HB651, and anti-HA [H28E3, and H17L2 (A7 CC #'s)]. The cytospins were washed several times with PD/1% BSA, and incubated with 1:200 dilution of biotinylated goat anti-mouse Ig [Boehringer Mannheim Biochemicals] for 45 min, followed by an HRP-Biotin-Avidin complex [Vector ABC kit,™ Burlingame, Calif.] for 30 min. Non-bound HRP was then washed off, and the HRP reaction product was developed with H$_2$O$^2$ and DAB [diaminobenzidine tetrahydrochloride, Polysciences, Warrington, Pa.].

Lymphocyte proliferation assays—Following infection with influenza virus, APCs were added in graded doses to 10⁵ T cells in 96 well flat bottomed plates Costar, Cambridge, MA1. Uninfected APCs served as controls. Proliferation was determined on days 5–6 with the addition of 4 uCi/ml of $^3$H-TdR for 12–16 h to triplicate microwells [mean cpm].

Results

We determined the extent to which human dendritic cells could be infected with influenza virus. Dendritic cells were isolated from buffy coat preparations as previously described, and pulsed with live influenza virus for 1 hour in serum free medium. Following multiple washes, immmunohistochemistry was employed to detect three viral proteins, NP, HA and NS1, within the cell, from 1 hour to 16 hours following infection [FIG. 1]. In addition, dendritic cells were compared to macrophages isolated from the same donor.

Dendritic cells failed to stain with isotype matched antibody OKT8 [FIG. 1A], but stained intensely with mAb to Class II [FIG. 1B]. At 16 hours following infection, NP staining was primarily localized to the nucleus of dendritic cells although there was clearly a cytoplasmic distribution in addition [FIG. 1C]. A diffuse distribution of HA, consistent with endogenous viral protein synthesis, was evident [FIGS. 1D and E]. Greater than 90% of the dendritic cells were infected by these criteria, with a viability of >90%. The NP and HA patterns of staining at 16 h after infection indicate extensive synthesis of viral proteins in the dendritic cells. Uninfected dendritic cells did not stain with any mAbs for viral specific proteins (data not shown].

Following just 1 hour of infection, dendritic cells expressed HA primarily in a granular pattern, suggesting that the virus is first contained within endocytic vacuoles [FIG. 1F]. Evidence of viral protein synthesis was also apparent in that there was diffuse cytoplasmic staining of a few cells, at this early time point [FIG. 1F, black arrows]. Pretreatment of dendritic cells with NH$_4$Cl prior to, during and following a virus pulse, blocked infection, i.e. few cells [<2%] stained with either anti-HA or anti-NP mAbs [data not shown]. These findings confirm that influenza requires an acidic compartment to deliver its genome to the cytoplasm and engage in viral specific protein synthesis. Macrophages were also highly susceptible to infection with influenza. The degree of infection was generally greater than 70% [FIGS. 1G and H]. After overnight incubation following infection, many cells died, and appeared to be phagocytosed by viable macrophages [FIG. 1G, black arrow]. In contrast, dendritic cells showed no change in viability for up to two days after infection.

Lymphocytes also were examined by immunolabeling for their ability to be infected by influenza virus, but none appeared to be as infected as dendritic cells. B cells and T cells were not susceptible to infection as assessed by staining with anti-HA and NP mAbs. T cell blasts generated with superantigens (SEA: staphylococcal enterotoxin), had a low level of infection (10–30% of the total T cell preparation), while EBV transformed cells had weak staining in 10–30% of the cells.

Relative efficacy of different influenza virus-pulsed APCs to induce T cell proliferative responses. Enriched populations of different APCs were pulsed with live influenza virus, and their ability to stimulate T cell proliferation was assessed. Virus pulsed dendritic cells were 30–50 fold more effective than macrophages and >200 fold more effective than B cells [FIG. 2]. Influenza specific responses were detectable even when 1 dendritic cell was used per 300 T cells. At these stimulator:responder ratios, influenza virus-pulsed macrophages and B cells were unable to induce T cells to proliferate [FIG. 2]. We noted that cultures containing significant numbers of infected macrophages e.g. at T cell:APC ratios of 10:1, or bulk cultures of PBMCs, there was striking toxicity and death of most cells, including T cells.

Dendritic cells are potent stimulators for the induction of influenza specific killer cell responses. We compared dendritic cells and macrophages for their capacity to generate human virus-specific CTL responses. The responding T cells were extensively depleted of APCs and added at a constant dose of $1 \times 10^6$ [see Materials and Methods]. APCs were then added in graded doses. In dozens of experiments, the T cells never generated lytic activity unless APCs were added, and the APCs themselves did not form lytic cells. Dendritic cells, if infected with influenza virus, generated significant CTL responses even when used at a 100:1 T cell/dendritic cell [FIG. 3A]. Significant killing was seen in the primary effector cell populations even at E:T ratios of 10:1 [FIG. 3B], or less [data not shown]. In contrast, macrophages were far less stimulatory, in the order of 100 fold or less, possibly due to the significant macrophage death observed following infection with virus. Since B cells are poor stimulators of the proliferative response to influenza, and do not get infected with the virus [see above], it is unlikely that contaminating B cells in our dendritic cell population account for the CTL that are generated. OKM1, an mAb directed towards the CD11b antigen, known to remove NK cell precursors (8), was used to deplete these cells from the starting T cell population. Thus the effector cell population used in these assays is composed of T cells. Experiments to be described below showed the killers to be CD8+CD4−. Most donors, >90%, could be primed with infected 2 dendritic cells, indicating that the majority of our donor pool has been exposed to influenza. Since CTL activity was measured on influenza A PR8-infected targets, a strain first identified in 1934, and the prevalent strains are A/Texas/36/91 and A/Beijing/32/92, the CTLs generated appear to be crossreactive, confirming other studies of human influenza-specific CTL (18).

Knowing that B cells do not contribute to CTL development, we next determined whether a partially purified preparation of dendritic cells, [i.e. omitting the metrizamide column for enrichment] was adequate for generating CTL responses to influenza. ER−, FcR− preparations are depleted of most T cells and monocytes and consist of approximately 5% dendritic cells, the remaining cells being primarily B cells. At T:APC ratios of 3:1 or 10:1, significant CTL responses were apparent [FIG. 4]. This corresponds to a T:dendritic cell ratio of 60:1 to about 180:1. ER−, FcR− cells were used as stimulators for all subsequent experiments, in T:APC ratios varying from 3:1 to 5:1. These partially enriched populations [a] suffice to provide the cultures with dendritic cells in the 1.5% range, [b] lack inhibitory monocytes, and [c] are straightforward to prepare.

To ascertain when lytic activity was optimal, we measured CTL development over the course of 9 days. Lytic activity peaked at day 7 [FIG. 5], consistent with other studies (18) with little variation from donor to donor. At this time, microscopic examination routinely showed the development of large cell clusters and released T cell blasts, as is characteristic of dendritic cell-mediated T cell responses in vitro (9). Occasionally, assays were done on day 8 if the clusters seemed slow to develop, and blast release delayed.

CD8+ T cells are the principal CTLs induced with infected dendritic cells. To establish the types of influenza-specific effector cells in our system, we stimulated bulk T cells with infected dendritic cells for 7 days and then separated the populations into CD4+ and CD8+ subsets. The cultures were stained with CD4-FITC and CD8-PE mAbs [Materials and Methods] and sorted on a FACSTAR™ into >98% pure CD4+ and CD8+ populations. Unseparated as well as sorted cells were then evaluated for lytic activity. Table I shows the data from three individual experiments. Influenza specific lytic activity was seen in two populations: bulk T cells and purified CD8+ T cells. CD4+ T cells failed to demonstrate any-lytic activity.

TABLE I

% SPECIFIC LYSIS OF MACROPHAGE TARGETS

| Responding T cells | Infection of APCS | Expt. 1 Mφ (−) | Expt. 1 Mφ FLU | Expt. 2 Mφ (−) | Expt. 2 Mφ FLU | Expt. 3 Mφ (−) | Expt. 3 Mφ FLU |
|---|---|---|---|---|---|---|---|
| Bulk | (−) | 0 | 0 | 0 | 0 | 2 | 4 |
|  | FLU | 0 | 25 | 0 | 42 | 9 | 51 |
| CD4+ | (−) | 0 | 0 | 0 | 0 | 4 | 8 |
|  | FLU | 0 | 0 | 0 | 0 | 4 | 9 |
| CD8+ | (−) | 3 | 7 | 0 | 0 | 3 | 9 |
|  | FLU | 2 | 37 | 0 | 57 | 16 | 54 |
| E: T ratio* |  |  | 40:1 |  | 40:1 |  | 50:1 |

Figure Legend for Table I. Influenza virus-specific CTL in bulk cultures are CD8+ CD4−. Purified T cells were stimulated with partially enriched populations of uninfected or influenza virus-infected dendritic cells at T:APC ratios of 3:1. After 7 days of culture, the T cells were stained with CD4-FITC and CD8-PE mAbs and sorted on a Facstar Plus™. The CD4+ and CD8+ populations were >98% pure. Lytic activity of each population was measured on infected syngeneic monocyte targets. Uninfected dendritic cells failed to stimulate influenza specific CTL. Three individual experiments are shown. *In expt. 1, the E:T ratio in the CD8+ T cell group was 30:1.

In general the CD8+ cells were enriched for lytic activity compared to the bulk T cells [Table 1 expt's 1 and 2]. FACs analyses of the stimulated cultures contained many enlarged T blasts and most of the enlarged cells were CD8+; few CD4+ cells appeared to enlarge in these cultures [FIG. 6].

To ascertain whether dendritic cell-induced $CD^8+$, influenza-specific CTLs were Class I restricted, we evaluated responses generated in two individuals who differed at Class I loci but shared Class II specificities [DRw52, DQw1]. Donor "A" demonstrated significant lytic activity against syngeneic infected macrophage targets [FIG. 7], but lesser activity against Class I mis-matched targets [donor B macrophage targets]. Likewise, donor zB" effector cells lysed syngeneic but not allogeneic ["A"] targets. The small degree of crossreactivity seen in the case of A effectors vs. B targets may be due to unspecified but shared Class I antigens, or possibly, the development of CD4+ mediated CTL activity, which has been described in cloned human populations (31,32). However, the latter is less likely given that no CD4+ CTLs are generated in our system [see below].

Purified CD4+ and CD8+ T cells respond to influenza virus-inected dendriotic cells. The observation that few CD4+ T cells seemed to be undergoing proliferation was surprising, since their role as helper cells for influenza virus-specific CTL responses is evident in mouse cultures (26). Also human CD4+ T cell clones with lytic activity have been described (31,32). To determine whether CD4+ T cells could respond to influenza virus-infected APCS, we used cell sorting to purify CD4+ and CD8+ T cells prior to T cell stimulation. Bulk, sorted CD4+, or CD8+ T cells, and a combination of both sorted populations, were tested in a standard proliferation assay for responsiveness to influenza virus-infected ER-,FcR-cells. All four groups were able to mount proliferative responses to these APCs [FIG. 8]. The most prominent response was demonstrated by the CD8+ T cells [note the lower background], compared to either bulk or CD4+ T cells. The extent of these responses were generally similar at several time points tested.

When CTL responses from these populations were measured, two striking observations were made. First, sorted CD8+ T cells developed CTL activity without a requirement for CD4+ T cells [FIG. 9]. These observations are reminiscent of human alloreactive responses, where CD4+ helper cells are not required for the generation of CD8+ CTL if dendritic cells are the APCs (8). Second, CD4+ T cells also developed lytic activity, but only in the absence of CD8+ T cells. We confirmed that the sorted populations were >98% pure at the termination of the 7 day induction period. Thus contamination of the CD8+ T cells with CD4+ T cells, or vice versa, does not account for these results. It is more likely that CD4+ T cells only exhibit the capacity to become CTLs, when few or no CD8+ T cells are present.

DISCUSSION

Experimental conditions for the generation of human CD8+ CTLs. To generate CD8+ CTLs against infectious agents in cultures of human T cells, one commonly uses unseparated populations of PBMCs and/or repeated stimulation in the presence of exogenous lymphokines like IL-2 (4,13,14,17–22). These requirements for CD8+ CTL development stand in contrast to CD4+ T cell responses, which often are detected within 3–5 days of culture without exogenous lymphokines. Furthermore, the primary APCs that induce CTL responses in human T cell cultures have not been well characterized.

Our results demonstrate that for the first time, strong influenza virus-specific CTLs can be induced using virus-infected dendritic cells as APCs. Partially enriched dendritic cells, which are straightforward to isolate, suffice for the development of CTLs. Our data which demonstrates indication of CTL's with relatively little proliferation, is particularly surprising in view of-prior reports of human dendritic cell induction data.

Four features distinguish our system for generating CTLs from the bulk culture systems that have been used previously. First, only a few dendritic cells (0.5–1% suffice) are required to generate highly potent CTL, as demonstrated by the fact that killing is evident at E:T ratios of 1.5:1 [FIG. 5]. Such efficacy has not been described in CTLs generated from cultures of bulk PBMCs (13,14,18,21). Second, depletion of monocytes is necessary to remove potential inhibitory and toxic effects on the effector cells. In attempts to generate CTLs from unseparated PBMCS, we often observed significant cell death that prohibited killer cell development. This was likely secondary to cytopathic effects of viral infection in monocytes as described [FIG. 1H]. PBMCs contain about 1% dendritic cells (34), and an Iat cell is known to be required for the generation of influenza virus-specific CTL in bulk PBMC culture systems (18). We suggest that these small numbers of dendritic cells are sufficient to permit CTL development in circumstances where few monocytes are present or become infected. Third, while monocytes do not induce CTLs effectively, they serve as efficient targets in short term chromium release assays (5 hours). During this time interval, a majority of monocytes express viral proteins as demonstrated by immunohistochemistry [data not shown]. In contrast, standard target cells e.g. B cell lines or PHA- treated lymphocytes, have a low level of infection (10–30%) and are less efficient in our hands as targets. Fourth, effector cell populations are routinely depleted of NK cells. These cells, which are activated by dendritic cells in vitro to lyse tumor cell targets (8), may play a role in viral clearance. They are not ordinarily depleted in bulk culture systems, and therefore could potentially mask specific CTL measurement.

Antigen presenting cell requirements for the generation of influenza virus-specific CTLS. T cell mediated immunity develops in two stages. In the afferent phase, dendritic cells bearing antigen, initiate T-dependent responses from resting lymphocytes. Once activated the sensitized T lymphoblasts can interact with other APCs in the efferent phase, to induce a number of effector functions, e.g. B cell antibody synthesis (35), macrophage activation and IL-1 production (36). As demonstrated here with influenza virus, dendritic cells serve in a similar capacity to first induce the generation of CD8+ CTLs, which then acquire the ability to kill infected macrophage targets. These pathways for CTL generation are potentially important for the prevention of cell-cell spread of virus.

Several features may account for the observed differences between dendritic cells and monocytes in the induction of influenza CTLs. One appears to be the manner in which influenza virus infection is handled by these two types of APCs. Greater than 90% of dendritic cells expressed HA, NP and NS-1 within 16 hours and remained fully viable for >24 hours after infection. In sharp contrast, freshly isolated monocytes or week old cultured macrophages were infected to a lesser extent [<70%] but died within 16 hours of infection [FIG. 1]. In addition to influenza virus, dendritic cells are specialized APCs for the presentation of several other viruses to T cells, including HSV (30), Moloney leukemia virus (28), Sendai virus (28) in the mouse and HIV in humans (37). It is not known whether the efficacy of dendritic cells in part reflects better developed pathways for the handling of viral antigens e.g. efficient charging of MHC Class I and II molecules. The findings nevertheless are consistent with other studies showing that dendritic cells present microbial antigens [M. tuberculosis (38), Leishmania (39), staphylococcal enterotoxins (40)] efficiently to T cells.

Dendritic cells are also distinguished from APCs like monocytes and B cells in the efficiency with which they deliver signals to the TCR-CD3 complex on T cells. For example, occupancy of only 0.1% of dendritic cell surface Class II molecules with superantigen is sufficient to induce T cell proliferation (23). This is due, in part, to the fact that dendritic cells express and upregulate many accessory molecules that are critical during the initiation of T cell immune responses [e.g. MLR (41), superantigens (23)]. They include B7/BB1 [CD80], ICAM-1 [CD54] and LFA-3 [CD58], ligands for CD28, CD11a and CD2, respectively. (Although we have yet to study the role of these accessory molecules on dendritic cells in CTL induction, there is evidence that interaction of CD28 with its ligand is a critical element in the activation of cytotoxic CD8+ T cells (42). For example, murine Class I restricted CTLs to alloantigens can be generated in the absence of help from CD4+ T cells, provided a CD28-B7 interaction occurs in the induction phase (42).)) Furthermore, B7-transfected tumor cells can induce protective [CD8+ T cell mediated] anti-tumor responses in vivo when CD4+ T cells are absent (43,44).

Our results reported herein are consistent with dendritic cells being key accessories in CTL induction. Accordingly, one would, therefore, predict that these APCs should also be effective in the generation of CTL responses to other antigens [e.g. melanoma antigens, alloantigens] where B7 is known to amplify the T cell response (41,43,44). The CD28-B7/BB1 interaction provides a critical costimulatory mechanism for IL-2 gene expression (45–47). This would explain the CD4 helper independence of CTL induction by dendritic cells i.e. their ability to present antigen together with costimulatory molecules like B7/BB1 that enhance the production of IL-2.

Helper cells are not required for the Generation of CD8+ CTLs. Our results demonstrate resting human T cells extensively depleted of CD4+ cells can be induced by dendritic cells to develop influenza virus-specific cytolytic activity. As in bulk cultures of T cells, CTL activity is generated with relatively few dendritic cells [FIG. 9]. Dendritic cells also directly induce human and murine CD8+ T cells to develop cytotoxic activity in the MLR (8,48). In contrast to these findings, Nonacs et al (26) found that mouse dendritic cells were unable to induce influenza virus-specific CTL activity in purified CD8+ T cells, unless a source of CD4+ T cells or helper lymphokines was available. A key variable here may be the number of antigen-specific IL-2 producers in the primed CD8+ population. For example, the paucity of precursor T cells in the mouse [1:16,600 to 1:2,400 (49)] may be insufficient to generate enough lymphokine to amplify a CTL response. Also, far fewer murine dendritic cells [<20%, (26)] are capable of synthesizing viral proteins than human blood dendritic cells [>90%, FIG. 1].

There are now several examples of CTL development in the apparent absence of CD4 help in vivo. For example, elimination of CD4+ T cells in mice does not ablate resistance to ectromelia virus (50,51), LCMV or vaccinia virus (52), and tumors (43,44).

Extensive proliferation of CD8+ T cells in response to influenza virus-infected dendritic cells. The majority of T cells that proliferate to influenza virus antigens in: bulk cultures are CD8+. We made this observation in routine Facs analyses of stimulated cultures [FIG. 6], where most enlarged T cells stained with antibodies to CD8. Primary populations of human CD8+ T cells, depleted of CD4+ T cells, also proliferate extensively after exposure to influenza virus-infected dendritic cells. The proliferative responses were considerably greater when compared to bulk ortCD4+ T cell responses [FIG. 8]. Other than responses to MLR antigens (8), we are not aware of other systems where such extensive antigen-dependent, CDB blastogenesis takes place. In mice, following i.p. infection with LCMV, large increases in CD8+ T cells in the spleen as well as the peritoneum occur (53).

Influenza virus-specific CD4+ CTL are also generated by dendritic cells. Highly purified CD4+ cells can be induced by blood dendritic cells to proliferate and develop cytolytic activity [FIGS. 8 and 9]. However, it is necessary to remove the CD8+ T cells to observe both the blastogenesis and CTL responses. The reasons for this are unclear. We considered the possibility that in bulk cultures, CD8+ CTLs might kill the CD4+ cells. Alternatively, there might be selective inhibition of exogenous antigen presentation via the Class II pathway, as previously described for influenza virus infected-murine APCs (54). This seemed unlikely for two reasons. First, CD4+ T cells can respond directly to infected dendritic cells when separated from CD8+ T cells. Second, influenza virus-infected APCs could present PPD to M. tuberculosis-reactive CD4+ T cell clones as well as uninfected APCs [data not shown].

Influenza-specific CD4+ CTL have been described in both human and mouse systems (16,31,32). In contrast to CD8+ CTLs, CD4+ Class II-restricted CTLs lysed target cells treated with noninfectious influenza virus or purified HA preparations and Class II presentation was sensitive to lysosomotropic agents (16). These differences provided critical early evidence that MHC Class I and Class II restricted CTL depended upon divergent pathways for presentation of antigen. The role of CD4+ CTL, in viral clearance and recovery from infection, however, remains to be determined. Beta-2-microglobulin deficient [−/−] mice have few CD8+ T cells but can clear vaccinia virus and nonlethal HKx31 influenza A virus, and resist a low inoculation dose of PR8 (55), but recovery from lethal doses of the virulent strain seems to require the presence of CD8+ T cells (56). In contrast, beta-2-microglobulin deficient [−/−] mice infected with LCMV intracranially, develop CD4+CTL that mediate disease, similar to their CD8+ counterparts in infected normal strains (57).

EXAMPLE 2

Use of Non Replicating Influenza Virus Vector to Deliver Antigen to Dendritic Cells The methods and materials unless otherwise specified were the same as in Example 1

The following methods were used carry out the experiments shown in Table II.

Poorly infectious forms of influenza virus induce human CTL responses. 1. Influenza virus was used live, inactivated at 56° for 30 minutes in a water bath or inactivated with UV irradiation for 30 minutes by exposing it to shortwave UV radiation [254 nm] from a Mineralight UV lamp [UVGL 58; Ultraviolets Products, San Gabrial, Calif.] for 0 mins at a distance of 4 centimeters. 2. influenza virus-specific CTLs were generated as previously described. In brief, partially enriched preparations of blood dendritic cells [which suffice as potent APCs] were washed out of serum containing medium and infected with 1,000 HAU/ml of different forms of PR8 influenza virus for 1 hr at 37° C. The APCs were washed and resuspended in RPMI containing 5% human serum, 10 ug/ml gentamicin and 10 mM Hepes. The cells were added to bulk cultures of purified syngeneic T cells at a 3:1 ratio [representing a T:dendritic cell ratio of 200–60:1]. T cells were obtained from PBMCs by sheep erythrocyte resetting. They were depleted of contaminating monocytes by panning on gamma-globulin coated dishes. MHC class II + and NK cells were depleted by coating with mAbs 9.3C9 [ATCC HB 180], and 3G8 [gift of Dr. J. Unkeless] and OKMI [ATCC; CRL8026], respectively, followed by panning on petri dishes coated with goat anti-mouse IgG. After 7 days of stimulation, T cells were harvested and distributed in varying numbers to 96 well round bottom plates. CTL activity was measured using a standard 51Cr-release assay with infected or uninfected syngeneic monocytes as targets. Percent specific release was calculated from the formula: 100 x [[Release by CTL-spontaneous release]/[Total release—spontaneous release]]. Lysis of uninfected targets was <5% at all E/T ratios used [data not shown]. 3. A modified plaque forming assay was performed using trypsin-resistant MDCK-II cells. These were grown in 6-well-plates to almost monolayer density, washed once with RPMI and then inoculated with 0.33 ml of serially diluted virus preparations for 1 hr at 37° C. The cells were washed again and overlaid with 3 ml of a 0.6% agarose solution in RPMI (low melting point agarose, type L, Behringwerke, Marburg, Germany) with freshly added trypsin final conc. 2.5–5.0 ug/ml). Trypsin was needed for cleaving the hemagglutinin of budding virus to facilitate infection of neighboring cells. After 3 days, cultures were stained with 0.2% crystal violet solution containing 4% formaldehyde. Plaque forming units were counted from duplicate to triplicate samples and calculated as PFU/ml. Results are averages of 4–7 experiments. 4. Virus was titered in a standard hemagglutination assay. Round-bottomed 96 well plates were used to set up serial twofold dilutions of virus samples in 25 ul volumes. These were tested with an equal volume of 1% CRBC suspension and incubated for >30 min at RT. Hemagglutination titers are expressed as HAU/ml and are representative of 3–4 expts. 5. To determine fusion activity of virus preparations a hemolysis assay was performed according to Huang et al with a modified protocol. 70 ul of chicken red blood cells (CRBC, 20% v/v in PBS-d) was preincubated with 90 ul of virus preparation at RT for 10 min. A 7.5×volume of 0.1M sodium acetate buffer (pH 5.4) in saline was then added (bringing the CRBC to a final concentration of 1%). Following 10 min. at RT, the suspension was incubated at 37° C. for 20 min to induce fusion and subsequently hemolysis. Cell fragments were spun down (5000 rpm for 2 min) and the supernatant was measured for extinction of hemoglobin at 540 nm. In addition, spontaneous release SR (in buffer) and maximum release MR (SDS-induced, final concentration 0.015%) were determined to calculate % of hemoglobin release as ((O.D. sample—O.D. SR) x 100):(O.D. MR—O.D. SR).

To obtain information on the nature of the antigen needed for stimulating MHC Class I restricted responses, we first evaluated the ability of live versus inactivated forms of influenza virus to generate human influenza specific CTL responses. When pulsed with heat treated [56° C., 30 min] or UV inactivated influenza virus, dendritic cells generated CTL responses that were equally potent to those that developed in response to live virus [Table II].

TABLE II

| Influenza virus[1] | TL Response[2] (E:T ratio) | | | Viral titres[3] | Hemag-glutination[4] | Hemoly-sis[5] |
|---|---|---|---|---|---|---|
| | 50:1 | 15:1 | 5:1 | PFU/ml | (HAU/ml) | |
| Live | 31 | 21 | 8 | $6.4 \pm 2.2 \times 10^8$ | $1 - 2 \times 10^4$ | + |
| Heat Inactivated | 44 | 25 | 9 | $\leq 3 \times 10^2$ | $0.5 - 2 \times 10^4$ | + |
| UV Inactivated | 42 | 24 | 9 | $1.3 \pm 1 - 3 \times 10^4$ | $0.5 - 2 \times 10^4$ | + |

Whereas the heat and UV inactivated viruses demonstrated substantially reduced titres >10,000 fold less active virus as determined by plaque forming assay [$<3 \times 10^2$ and $1.3 \times 10^4$ PFU/ml, respectively], they had comparable hemagglutinating activity to the live virus, suggesting that the total amount of virus was not altered by inactivation treatments [Table II]. Influenza virus attaches to sialic acid residues on gycoconjugates on the cell surface via hemagglutinin, and is internalized by endocytosis. Escape from the endosome into the cytoplasm then ensues at acid pH, when the hemagglutinin undergoes a conformational change that permits fusion of the viral envelope with the endosomal membrane. Both heat inactivated (HI),and ultra violet (UV) inactivated forms of influenza retained this fusion capacity, since they could hemolyze chicken erythrocytes at acid pH [Table II].

The ability to induce CTL responses to heat inactivated forms of influenza virus appears to be restricted to dendritic cells, since macrophages were ineffective in this capacity [data not shown]. Dose response titrations demonstrate that, despite the substantial reduction in infectious titer of the heat inactivated virus, it retains the ability to induce CTL responses even at 10 HAU/ml, and the dose response curve is similar to that of live virus [FIG. 10A]. Immunohistochemistry was employed to determine the extent of infection in dendritic cells and macrophages, following overnight culture after a 1 hr pulse with live or heat inactivated virus. The influenza protein NP was evident in dendritic cells infected with 1000 HAU/ml of live virus, but not heat inactivated virus [FIG. 10B]. Similarly, HA could only be detected on dendritic cells exposed to live but not heat inactivated virus [data not shown]. Similar observations were made for macrophages [data not shown]. Collectively, the data in FIGS. 10A–B indicate that only small amounts of virus need be presented on dendritic cells to elicit human cytolytic responses.

Further experiments were done to characterize the attenuation of influenza virus with heat versus UV irradiation. Heat treatment of influenza virus at temperature greater than 56° destroyed the CTL inducing capacity of the virus [FIGS. 11A and 11B]. To determine whether the temperature affects the ability of the virus to fuse with membranes, a fusogenic assay was performed using chicken erythrocytes, as described in Table 1. At 60°, the virus can no longer lyse CRBC at an acid pH, possibly because the HA has been altered at these higher temperatures [data not shown]. Heat inactivated and UV virus were equally effective at inducing CTL responses [FIG. 11C and Table II]. Since allantoic fluid was used as the source of our virus preparations, we ascertained whether immunogenic viral protein or peptide fragments in the fluid might be responsible for the observed ability of inactivated virus to elicit CTL responses. Live and heat inactivated virus was adsorbed with CRBC, and the nonbound fraction [CRBC-] was pulsed onto dendritic cells to test for CTL inducing activity. The CRBC- preparation failed to generate CTL responses [FIG. 12A]. Furthermore, the ability of the CRBC- fraction to sensitize macrophage targets was also lost [FIG. 12B]. The CRBC- adsorbed fraction demonstrated virus activity in a TCID 50 assay [data not shown]. Thus the CTL responses generated by inactivated virus is due to whole virus and not contaminating viral antigens.

To establish the types of influenza-specific effector cells generated in response to heat inactivated virus, we stimulated bulk T cells with heat inactivated virus-infected dendritic cells for 7 days, and then separated the populations into CD4+ and CD8+ subsets. The cultures were stained with CD4- FITC and sorted on a Facstar into >98% pure CD4+ and CD8+ populations. Unstimulated T cells were evaluated in the same way. Sorted subsets as well as unseparated cells stimulated with the live virus infected dendritic cells were then tested for lytic activity. Influenza specific CTL activity was seen in two populations: purified CD8+ T cells and bulk T cells [FIG. 13]. Little activity was evident in the CD4+ subset. Similar data was obtained with T cell populations obtained after stimulation with dendritic cells pulsed with UV inactivated virus [data not shown].

Thus, as with live virus, CD8+CTLs are the principal CTLs induced with dendritic cells infected with inactivated virus.

To ascertain whether dendritic cells induced CD8+ influenza specific CTLs were Class I restricted, blocking experiments were performed with antibodies to Class I vs. Class II.

To determine whether purified CD8+ T cells could respond to dendritic cells infected with attenuated virus, CD8+ and CD4+ T cells were purified before T cell stimulation. Bulk, purified CD8+ and CD4+ cells were tested for responsiveness to dendritic cells pulsed with live or heat inactivated virus. Both the purified subsets developed CTL activity without a requirement for CD4+ T cells, as shown previously for live virus [FIG. 14]. CD4+ T cells also developed lytic activity, but only in the absence of CD8+ T cells. Thus, as for live virus, it seems the CD4+ T cells acquire the capacity to become CTLs when few CD8+ T cells are present.

T cells appear to recognize very small numbers of MHC—antigen complexes in order to become activated. Little is known, however, about the amount of antigen that is required or the efficiency with which it is handled, in order for those MHC-peptide complexes to be generated. Here we find that when dendritic cells are the antigen presenting cells, only small amounts of an attenuated virus need to be handled by the cell to elicit strong CTL responses. The CTL responses generated are as potent as those induced by nonattenuated virus. These results may having bearing on the ability of dendritic cells to initiate CLTs in other contexts like autoimmunity and tumor protection.

REFERENCES

1. Koup, R. A., C. A. Pikora, K. Luzuriaga, D. B. Brettler, E. S. Day, G. P. Mazzara, and J. L. Sullivan. 1991. Limiting dilution analysis of cytotoxic T lymphocytes to human immunodeficiency virus gag antigens in infected persons: in vitro quantitation of effector cell populations with p17 and p24 specificities. *J. Exp. Med.* 174:1593–1600.
2. Carmichael, A., X. Jin, P. Sissons, and L. Borysiewicz. 1993. Quantitative analysis of the human HIV-1 specific cytotoxic T lymphocyte 1CTL] response at different stages of HIV-1 infection: Differential CTL response to HIV-1 and Epstein-Barr virus in late disease. *J. Exp. Med.* 177:249–256.
3. Johnson, R. P., A. Trocha, T. M. Buchanan, and B. D. Walker. 1992. Identification of overlapping HLA Class I-restricted cytotoxic T cell epitopes in a conserved region of the human immunodeficiency virus type 1 envelope glycoprotein: Definition of minimum epitopes and analysis of the effects of sequence variation. *J. Exp. Med.* 175:961–971.
4. Riddell, S. R., K. S. Watanabe, J. M. Goodrich, C. R. Li, M. E. Agha, and P. D. Greenberg. 1992. Restoration of viral immunity in immunodeficient humans by the adoptive transfer of T cell clones. *Science* 257:238–241.
5. Hill, A. V. S., J. Elvin, A. C. Willis, M. Aidoo, C. E. M. Allsopp, F. M. Gotch, X. M. Gao, M. Takiguchi, B. M. Greenwood, A. R. M. Townsend, A. J. McHichael, and H. C. Whittle. 1992. Molecular analysis of the association of HLA-B53 and resistance to severe malaria. *Nature* 360:434–439.
6. Van Der Bruggen, P., C. Traversari, P. Chomez, C. Lurquin, E. De Plaen, B. Van Den Eynde, A. Knuth, and T. Boon. 1991. A gene encoding an antigen recognized by cytolytic T lymphocytes on a human melanoma. *Science* 254:1643–1647.
7. Brichard, V., A. Van Pel, T. Wolfel, C. Wolfel, E. De Plaen, B. Lethe', P. Coulie, and T. Boon. 1993. The tyrosinase gene codes for an antigen recognized by autologous cytolytic T lymphocytes on HLA-A2 melanomas. *J. Exp. Med.* 178:489–495.
8. Young, J. W. and R. M. Steinman. 1990. Dendritic cells stimulate primary human cytolytic lymphocyte responses in the absence of CD4+ helper T cells. *J. Exp. Med.* 171:1315–1332.
9. Steinman, R. M. 1991. The dendritic cell system and its role in immunogenicity. *Ann. Rev. Immunol.* 9: 271–296.
10. Wiley, D. C., I. A. Wilson, and J. J. Skehel. 1981. Structural identification of the antibody-binding sites of Hong Kong influenza hemagglutinin and their involvement in antigenic variation. *Nature* 289:373.
11. Holt, P. C., M. A. Schon-Hegrad, and J. Oliver. 1987. MHC Class II antigen-bearing dendritic cells in pulmonary tissues of the rat. Regulation of antigen presentation activity by endogenous macrophage populations. *J. Exp. Med.* 167:262–274.
12. Schon-Hegrad, M. A., J. Oliver, P. G. McMenamin, and P. G. Holt. 1991. Studies on the density, distribution, and surface phenotype of intraepithelial Class II major histocompatibility complex antigen [Ia]-bearing dendritic cells [DC] in the conducting airways. *J. Exp. Med.* 173:1345–1356.
13. McMichael, A. J., F. M. Gotch, G. R. Noble, and P. A. S. Beare. 1983. Cytotoxic T-cell immunity to influenza. *N. Engl. J. Med.* 309:13–17.
14. Townsend, A. R. M., F. M. Gotch, and J. Davey. 1985. Cytotoxic T cells recognize fragments of the influenza nucleoprotein. *Cell* 42:457–467.
15. Townsend, A. R. M., J. Rothbard, F. M. Gotch, G. Bahadur, D. Wraith, and A. J. McHichael. 1986. The epitopes of influenza nucleoprotein recognized by cytotoxic T lymphocytes can be defined with short synthetic peptides. *Cell* 44:959–968.
16. Morrison, L. A., A. E. Lukacher, V. L. Braciale, D. P. Fan, and T. J. Braciale. 1986. Differences in antigen presentation to MHC Class I- and Class II-restricted influenza virus-specific cytolytic T lymphocyte clones. *J. Exp. Med.* 163:903–921.
17. Carreno, B. M., R. W. Anderson, J. E. Coligan, and W. E. Biddison. 1990. HLA-B37 and HLA-A2.1 molecules bind largely nonoverlapping sets of peptides. *Proc. Natl. Acad. Sci. USA* 87:3420–3424.
18. McHichael, A. J. and B. A. Askonas. 1978. Influenza virus-specific cytotoxic T cells in man; induction and properties of the cytotoxic cell. *Eur. J. Immunol.* 8:705–711.
19. Gotch, F., J. Rothbard, K. Howland, A. Townsend, and A. McHichael. 1987. Cytotoxic T lymphocytes recognize a fragment of influenza virus matrix protein in association with HLA-A2. *Nature* 326:881.
20. McMichael, A. J., F. M. Gotch, and J. Rothbard. 1986. HLA B37 determines an influenza A virus nucleoprotein epitope recognized by cytotoxic T lymphocytes. *J. Exp. Med.* 164:1397–1406.
21. Sutton, J., S. Rowland-Jones, U. Rosenberg, D. Nixon, F. Gotch, X.-M. Gao, N. Murray, A. Spoonas, P. Driscoll, M. Smith, A. Willis, and A. McHichael. 1993. A sequence pattern for peptides presented to cytotoxic T lymphocytes by HLA B8 revealed by analysis of epitopes and eluted peptides. *Eur. J. Immunol.* 23:447–453.
22. Bowness, P., P. A. H. Moss, J. I. Bell, and A. J. McHichael. 1993. Conservation of T cell receptor usage by HLA B27-restricted influenza-specific cytotoxic T lymphocytes suggests a general pattern for antigen-specific major histocompatibility complex Class I-restricted responses. *Eur. J. Immunol.* 23:1417–1421.
23. Bhardwaj, N., J. W. Young, A. J. Nisanian, J. Baggers, and R. M. Steinman. 1993. Small amounts of superantigen, when presented on dendritic cells, are sufficient to initiate T cell responses. *J. Exp. Med.* 178:633–642.
24. Young, J. W. and R. M. Steinman. 1988. Accessory cell requirements for the mixed leukocyte reaction and polyclonal mitogens, as studied with a new technique for enriching blood dendritic cells. *Cell. Immunol.* 111:167–182.
25. Freudenthal, P. S. and R. M. Steinman. 1990. The distinct surface of human blood dendritic cells, as observed after an improved isolation method. *Proc. Natl. Acad. Sci. USA* 87:7698–7702.
26. Nonacs, R., C. Humborg, J. P. Tam, and R. M. Steinman. 1992. Mechanisms of mouse spleen dendritic cell function in the generation of influenza-specific, cytolytic T lymphocytes. *J. Exp. Med.* 176:519–529.
27. Young, J. W. and R. M. Steinman. 1987. Mononuclear phagocytes as targets for cytolytic T lymphocytes. *J. Immunol. Meth.* 100:99–105.
28. Kast, W. M., C. J. P. Boog, B. O. Roep, A.C. Voordouw, and C. J. M. Melief. 1988. Failure or success in the restoration of virus-specific cytotoxic T lymphocyte response defects by dendritic cells. *J. Immunol.* 140:3186–3193.
29. Macatonia, S. E., P. M. Taylor, S. D. Knight, and B. A. Askonas. 1989. Primary stimulation by dendritic cells induces anti-viral proliferative and cytotoxic T cell responses in vitro. *J. Exp. Med.* 169:1255–1264.
30. Hengel, H., M. Lindner, H. Wagner, and K. Heeg. 1987. Frequency of herpes simplex virus-specific murine cytotoxic T lymphocyte precursors in mitogen-and antigen-driven primary in vitro T cell responses. *J. Immunol.* 139 4196–4202.
31. Kaplan, D. R., R. Griffith, V. L. Braciale, and T. J. Braciale. 1984. Influenza virus-specific human cytotoxic T cell clones: Heterogeneity in antigenic specificity and restriction by Class II MHC products. *Cell. Immunol.* 88:193–206.
32. Cerundolo, V., A. G. D. Tse, R. D. Salter, P. Parham, and A. Townsend. 1991. CD8 independence and specificity of cytotoxic T lymphocytes restricted by HLA-Aw68.1. *Proc. Roy. Soc. London ser B* 244:169–177.
33. Knight, S. C. and S. E. Macatonia. 1988. Dendritic cells and viruses. *Immunol. Letters* 19:177–182.
34. O'Doherty, U., R. M. Steinman, P. Peng, P. U. Cameron, S. Gezelter, I. Kopeloff, W. J. Swiggard, M. Pope, and N. Bhardwaj. 1993. Dendritic cells freshly isolated from human blood express CD4 and mature into typical immunostimulatory dendritic cells after culture in monocyte-conditioned medium. *J. Exp. Med.* 178:1067–1078.
35. Inaba, K. and R. M. Steinman. 1985. Protein-specific helper T lymphocyte formation initiated by dendritic cells. *Science* 229:475–479.
36. Bhardwaj, N., L. L. Lau, S. M. Friedman, M. K. Crow, and R. M. Steinman. 1989. Interleukin 1 production during accessory cell-dependent mitogenesis of T lymphocytes. *J. Exp. Med.* 169:1121–1136.
37. Cameron, P. U., P. S. Freudenthal, J. M. Barker, S. Gezelter, K. Inaba, and R. M. Steinman. 1992. Dendritic cells exposed to human immunodeficiency virus type-1 transmit a vigorous cytopathic infection to CD4+ T cells. *Science* 257:383–387.
38. Pancholi, P., R. M. Steinman, and N. Bhardwa;. 1992. Dendritic cells efficiently immunoselect mycobacterial-reactive T cells in human blood, including clonable antigen-reactive precursors. *Immunol.* 76:217–224.
39. Moll, H., H. Fuchs, C. Blank, and M. Rollinghoff. 1993. Langerhans cells transport Leishmania major from the infected skin to the draining lymph node for presentation to antigen-specific T cells. *Eur. J. Immunol.* 23:1595–1601.
40. Bhardwaj, N., S. M. Friedman, B. C. Cole, and A. J. Nisanian. 1992. Dendritic cells are potent antigen-presenting cells for microbial superantigens. *J. Exp. Med.* 175:267–273.
41. Young, J. W., L. Koulova, S. A. Soergel, E. A. Clark, R. M. Steinman, and B. Dupont. 1992. The B7/BB1 antigen provides one of several costimulatory signals for the activation of CD4+ T lymphocytes by human blood dendritic cells in vitro. *J. Clin. Invest.* 90:229–237.
42. Harding, F. A. and J. P. Allison. 1993. CD28-B7 interactions allow the induction of CD8+ cytotoxic T lymphocytes in the absence of exogenous help. *J. Exp. Med.* 177:1791–1796.
43. Townsend, S. E. and J. P. Allison. 1993. Tumor rejection after direct costimulation of CD8+ T cells by B7-transfected melanoma cells. *Science* 259:368–370.
44. Chen, L., S. Ashe, W. A. Brady, I. Hellstrom, K. E. Hellstrom, J. A. Ledbetter, P. McGowan, and P. S. Linsley. 1992. Costimulation of antitumor immunity by the B7 counterreceptor for the T lymphocyte molecules CD28 and CTLA-4. *Cell* 71:1093–1102.
45. Fraser, J. D., M. E. Newton, and A. Weiss. 1992. CD28 and T cell antigen receptor signal transduction coordinately regulate interleukin 2 gene expression in response to superantigen stimulation. *J. Exp. Med.* 175:1131–1134.
46. Fraser, J. D., B. A. Irving, G. R. Crabtree, and A. Weiss. 1991. Regulation of interleukin-2 gene enhancer activity by the T cell accessory molecule CD28. *Science* 251:313–316.
47. Thompson, C. B., T. Lindsten, J. A. Ledbetter, S. L. Kunkel, H. A. Young, S. G. Emerson, J. M. Leiden, and. C. H. June. 1989. CD28 activation pathway regulates the production of multiple T cell-derived lymphokines/cytokines. *Proc. Natl. Acad. Sci. USA* 86:1333–1337.
48. Inaba, K., J. W. Young, and R. M. Steinman. 1987. Direct activation of CD8+ cytotoxic T lymphocytes by dendritic cells. *J. Exp. Med.* 166:182–194.
49. Wysocka, M. and J. P. Bennink. 1988. Limiting dilution analysis of memory cytotoxic T lymphocytes specific for individual influenza virus gene products. *Cell. Immunol.* 112:425–429.
50. Buller, M. L., K. L. Holmes, A. Hugin, T. N. Frederickson, and H. C. Morse III. 1987. Induction of cytotoxic T-cell response in vivo in the absence of CD4 helper cells. *Nature* 328:77–79.
51. Buller, R. M. L., K. L. Holmes, A. Hugin, T. N. Frederickson, and H. C. Morse III. 1987. Induction of cytotoxic T-cell responses in vivo in the absence of: CD4 helper cells. *Nature* 328:77–79.
52. Rahemtulla, A., W. P. Fung-Leung, M. W. Schilham, T. M. Kundig, S. R. Sambhara, A. Narendran, A. Arabian, A. Wakeham, C. J. Paige, R. M. Zinkernagel, R. G. Miller, and T. W. Mak. 1991. Normal development and function of CD8+ cells but markedly decreased helper cell activity in mice lacking CD4. *Nature* 353:180–184.
53. Lynch, D. H. and R. E. Miller. 1994. Interleukin 7 promotes long-term in vitro growth of antitumor cytotoxic T lymphocytes with immunotherapeutic efficacy in vivo. *J. Exp. Med.* 179:31–42.

54. Domanico, S. Z. and S. K. Pierce. 1992. Virus infection blocks the processing and presentation of exogenous antigen with the major histocompatibility complex Class II molecules. *Eur. J. Immunol.* 22:2055–2062.
55. Eichelberger, M., W. Allan, M. Zijlstra, R. Jaenisch, and P. C. Doherty. 1991. Clearance of influenza virus respiratory infection in mice lacking Class I major histocompatibility complex-restricted CD8+ T cells. *J. Exp. Med.* 174:875–880.
56. Bender, B. S., T. Croghan, L. Zhang, and P. A. Small Jr.. 1992. Transgenic mice lacking Class I major histocompatibility complex-restricted T cells have delayed viral clearance and increased mortality after influenza virus challenge. *J. Exp. Med.* 175:1143–1145.
57. Muller, D., B. H. Koller, J. L. Whitton, K. E. LaPan, K. K. Brigman, and J. A. Frelinger. 1992. LCMV-specific, Class II-restricted cytotoxic T cells in pz-microglobulin-deficient mice. *Science* 255:1576–1578.
58. Kuzu, H., Y. Kuzu, H. Zaghouani, and C. Bona. 1993. In vivo priming effect during various stages of ontogeny of an influenza A virus nucleoprotein peptide. *Eur. J. Immunol.* 23:1397–1400.
59. Aichele, P., H. Hengartner, R. M. Zinkernagel, and M. Schulz. 1990. Antiviral cytotoxic T cell response induced by in vivo priming with a free synthetic peptide. *J. Exp. Med.* 171:1815–1820.
60. Gao, X. M., B. Zheng, F. Y. Liew, S. Brett, and J. Tite. 1991. Priming of influenza virus-specific cytotoxic T lymphocytes vivo by short synthetic peptides. *J. Immunol.* 147:3268–3273.
61. Schulz, M., R. M. Zinkernagel, and H. Hengartner. 1991. Peptide-induced antiviral protection by cytotoxic T cells. *Proc. Natl. Acad. Sci. USA* 88:991–993.
62. Deres, K., H. Schild, K. -H. Wiesmuller, G. Jung, and H. -G. Rammensee. 1989. In vivo priming of virus-specific cytotoxic T lymphocytes with synthetic lipopeptide vaccine. *Nature* 342:561–564.
63. Takahashi, H., T. Takeshita, B. Morein, S. Putney, R. N. Germain, and J. A. Berzofsky. 1990. Induction of CD8+ cytotoxic T cells by immunization with purified HIV-1 envelope protein in ISCOMs. *Nature* 344:873–875.
64. Uatari, E., B. Dietzschold, G. Szokan, and E. Heber-Katz. 1987. A synthetic peptide induces long-term protection from lethal infection with herpes simplex virus 2. *J. Exp. Med.* 165:459–470.
65. Nair, S., F. Zhou, R. Reddy, L. Huang, and B. T. Rouse. 1992. Soluble proteins delivered to dendritic cells via pH-sensitive liposomes induce primary cytotoxic T lymphocyte responses in vitro. *J. Exp. Med.* 175:609–613.
66. Ulmer, J. B., J. J. Donnelly, S. E. Parker, G. H. Rhodes, P. L. Felgner, V. J. Dwarki, S. H. Gromkowski, R. R. Deck, C. M. DeWitt, A. Friedman, L. A. Hawe, K. R. Leander, D. Martinez, H. C. Perry, J. W. Shiver, D. L. Montgemery, and M. A. Liu. 1993. Heterologous protection against influenza by injection of DNA encoding a viral protein. *Science* 259:1745–1749.
67. Fuchs, E. J. and P. Matzinger. 1992. B cells turn off virgin but not memory T cells. *Science* 258:1156–1159.
68. Inaba, K., J. P. Metlay, M. T. Crowley, and R. M. Steinman. 1990. Dendritic cells pulsed with protein antigens in vitro can prime antigen-specific, MHC-restricted T cells in situ. *J. Exp. Med.* 172:631–640.
69. Inaba, K., M. Inaba, M. Naito, and R. M. Steinman. 1993. Dendritic cell progenitors phagocytose particulates, including Bacillus Calmette-Guerin organisms, and sensitize mice to mycobacterial antigens in vivo. *J. Exp. Med.* 178:479–488.
70. Takahashi, H., Y. Nakagawa, K. Yokomuro, and J. A. Berzofsky. 1993. Induction of CD8+ cytotoxic T lymphocytes by immunization with syngeneic irradiated HIV-1 envelope derived peptide-pulsed dendritic cells. *Int. Immunol.* 5: 849–857.

We claim:

1. Antigen presenting human dendritic cells prepared according to the method of:
   contacting, in vitro, proliferating or non-proliferating human dendritic cells with a nonreplicating viral vector comprising a gene sequence encoding an antigen which antigen is processed by said dendritic cells, and wherein said processed antigen is presented on the surface of said dendritic cells, and wherein said dendritic cells activate cytotoxic T cell responses that are at least as potent as those that develop in response to live virus.

2. The antigen presenting dendritic cells according to claim 1 wherein said dendritic cells are infected with a nonreplicating influenza virus.

3. The antigen presenting dendritic cells according to claim 1 wherein said dendritic cells induce cytotoxic T cells with a dose response curve similar to that obtained with dendritic cells infected with live virus.

4. The antigen presenting dendritic cells according to claim 1 wherein said dendritic cells induce cytotoxic T cells at a dose of about 10 HAU/ml.

5. The antigen presenting dendritic cells according to claim 1 wherein said dendritic cells induce lymphocytes at a ratio of about 1 dendritic cell to about 10 to 100 lymphocytes.

6. The antigen presenting dendritic cells according to claim 1 wherein said dendritic cells induce lymphocytes at ratio of about 1 dendritic cell to about 100 lymphocytes.

7. An in vitro cell mixture comprising activated antigen-specific human cytotoxic T lymphocytes and dendritic cells which express on their surface a processed antigen encoded by a nonreplicating viral vecto , and wherein the cytotoxic T lymphocytes are activated by said processed antigen on said dendritic cells, and wherein said dendritic cells activate cytotoxic T cell responses that are at least as potent as those that develop in response to live virus.

8. The cytotoxic T lymphocytes of claim 7 wherein the cytotoxic T lymphocytes are contacted with dendritic cells expressing influenza virus antigen.

9. A pharmaceutical composition comprising antigen presenting human dendritic cells prepared according to the method of:
   contacting, in vitro, proliferating or non-proliferating human dendritic cells with a nonreplicating viral vector comprising a gene sequence encoding an antigen, which antigen is processed by said dendritic cells to produce a processed antigen which is presented on the surface of said dendritic cells, and wherein said dendritic cells activate cytotoxic T cell responses that are at least as potent as those that develop in response to live virus, and a pharmaceutically acceptable carrier.

10. A pharmaceutical composition comprising activated antigen-specific human cytotoxic T lymphocytes and dendritic cells which express on their surface a processed antigen encoded by a nonreplicating viral vector, and wherein the cytotoxic T lymphocytes are activated by said processed antigen on said dendritic cells, and wherein said dendritic cells activate cytotoxic T cell responses that are at least as potent as those that develop in response to live virus, and a pharmaceutically acceptable carrier.

11. The pharmaceutical composition according to claim 10 wherein the dendritic cells are subsequently removed.

* * * * *